(12) United States Patent
Nordgren et al.

(10) Patent No.: US 11,918,503 B2
(45) Date of Patent: Mar. 5, 2024

(54) EASY ON/EASY OFF CLIPS OR CLAMPS FOR MOUNTING MASK TO BODY PART FIXATION DEVICE

(71) Applicant: Medtec LLC, Orange City, IA (US)

(72) Inventors: Gregory Nephi Nordgren, Saratoga Springs, UT (US); William Louis Barnat, Mount Holly, NJ (US); Renaud Durand, Iowa City, IA (US); Keith Van Voorst, Hull, IA (US)

(73) Assignee: MEDTEC LLC, Orange City, IA (US)

( * ) Notice: Subject to any disclaimer, the term of this patent is extended or adjusted under 35 U.S.C. 154(b) by 655 days.

(21) Appl. No.: 16/363,441

(22) Filed: Mar. 25, 2019

(65) Prior Publication Data
US 2019/0290471 A1    Sep. 26, 2019

Related U.S. Application Data

(60) Provisional application No. 62/648,011, filed on Mar. 26, 2018.

(51) Int. Cl.
*A61F 5/37*     (2006.01)
*A61B 6/04*     (2006.01)
(Continued)

(52) U.S. Cl.
CPC .......... *A61F 5/3707* (2013.01); *A61B 6/0421* (2013.01); *A61B 6/0428* (2013.01);
(Continued)

(58) Field of Classification Search
CPC ........ A61F 5/3707; A61F 5/3769; A61F 5/37; A61B 6/0421; A61B 6/0428;
(Continued)

(56) References Cited

U.S. PATENT DOCUMENTS 3,957,262 A    5/1976  McReynolds
3,963,382 A *  6/1976  Patton ................... F04D 29/646
                                                74/609
(Continued)

FOREIGN PATENT DOCUMENTS

CA        2633680 A1    7/2007
JP     2002345906 A    12/2002
(Continued)

OTHER PUBLICATIONS

PCT International Search Report and Written Opinion issued for the corresponding international application No. PCT/ JS2019/023850, dated Jul. 31, 2019, 18 pages.
(Continued)

*Primary Examiner* — Alireza Nia
*Assistant Examiner* — Daniel A Miller
(74) *Attorney, Agent, or Firm* — Snyder, Clark, Lesch & Chung, LLP

(57) ABSTRACT

A structure includes a first frame having a shape to fit around, or over, a body part, the first frame further comprising a first surface configured to dock with a docking surface of a second frame configured to receive and support the body part. The structure also includes a material attached to the first frame for fitting to the body part; and at least one attachment mechanism coupled to the first frame and configured to attach the first frame to the second frame when the first surface of the first frame is docked with the docking surface of the second frame, wherein the at least one attachment mechanism is configured to flex or pivot, relative to a lateral edge of the first frame, to attach the first frame to the second frame when the first surface of the first frame is docked with the docking surface of the second frame.

22 Claims, 31 Drawing Sheets

(51) Int. Cl.
*A61B 90/18* (2016.01)
*A61N 5/10* (2006.01)

(52) U.S. Cl.
CPC .............. *A61N 5/10* (2013.01); *A61N 5/1049* (2013.01); *A61B 90/18* (2016.02); *A61N 2005/1097* (2013.01)

(58) Field of Classification Search
CPC ......... A61B 6/0492; A61B 6/04; A61B 6/032; A61B 90/18; A61B 90/14; A61B 2090/101; A61B 5/70; A61B 5/702; A61B 5/055; A61N 5/10; A61N 5/1049; A61N 2005/1097; A61N 2005/1087; A61G 13/101; A61G 2210/50; A61G 7/07; A61G 7/072; A61G 13/121; A47C 7/383; Y10T 292/20; Y10T 292/202; Y10T 292/225; Y10T 292/42; Y10T 292/444; Y10T 292/11; Y10T 292/30; Y10T 292/38; F04D 29/646; F04D 29/64; F04D 29/60
USPC .... 128/845; 5/600, 601, 621, 622, 636, 637; 600/410, 415
See application file for complete search history.

(56) References Cited

U.S. PATENT DOCUMENTS

| | | | |
|---|---|---|---|
| 4,504,050 A | | 3/1985 | Osborne |
| 5,370,117 A | | 12/1994 | McLaurin, Jr. |
| 5,553,112 A | | 9/1996 | Hardy et al. |
| 5,566,681 A | | 10/1996 | Manwaring et al. |
| 5,595,191 A | | 1/1997 | Kirk |
| 5,702,406 A | * | 12/1997 | Vilsmeier .............. A61B 90/18 128/845 |
| 5,775,337 A | * | 7/1998 | Hauger .................. A61B 90/14 128/869 |
| 5,782,244 A | | 7/1998 | Kostich |
| 5,800,353 A | | 9/1998 | McLaurin, Jr. |
| 5,848,449 A | * | 12/1998 | Hauger ................ A61B 6/0421 5/601 |
| 6,698,045 B1 | | 3/2004 | Coppens et al. |
| 7,073,508 B2 | | 7/2006 | Moyers |
| 7,103,930 B1 | | 9/2006 | Addesso-Dodd |
| 7,290,548 B2 | | 11/2007 | Ungemach et al. |
| 7,802,576 B2 | | 9/2010 | Cuypers et al. |
| 8,100,132 B2 | | 1/2012 | Markstroem |
| 8,567,405 B2 | | 10/2013 | Am et al. |
| 2002/0038659 A1 | | 4/2002 | Al-kassim |
| 2004/0159325 A1 | | 8/2004 | Korver et al. |
| 2009/0293883 A1 | * | 12/2009 | Arn ........................ A61B 90/14 128/845 |
| 2010/0000549 A1 | | 1/2010 | Nieberding |
| 2015/0047652 A1 | | 2/2015 | De Mooij |
| 2015/0053213 A1 | | 2/2015 | Nieberding |
| 2015/0096570 A1 | | 4/2015 | Noras |
| 2015/0202073 A1 | * | 7/2015 | Zacharopoulos ..... A61F 5/3707 128/845 |
| 2016/0095739 A1 | | 4/2016 | Coppens et al. |
| 2016/0206395 A1 | * | 7/2016 | Coppens ................ A61B 90/18 |
| 2016/0213337 A1 | | 7/2016 | Coppens et al. |
| 2018/0008840 A1 | * | 1/2018 | Van Voorst .............. A61N 5/10 |

FOREIGN PATENT DOCUMENTS

| | | |
|---|---|---|
| JP | 2009000321 A | 1/2009 |
| WO | 2016124232 A1 | 8/2016 |

OTHER PUBLICATIONS

High-Accuracy Localization Using Implanted Fiducials—by Northwest Medical Physics Equipment, Lynnwood, WA. Tech Times, vol. 8, Issue 2, Fall 2002, 2 pages.
Specialty systems to further enhance the benefits of the Type-S. Advanced Patient Positioning and Fixation. Astro 2004. Medtec. 2 pages.
Uni-frame head & neck immobilization system. Med-Tec Inc. Medtec 2003 Catalog. 3 pages.
Civco: Shell, Prone Head Support. Dwg. No. MT-202-15. 2009, 1 page.
Freedom Prone Immobilization System. CDR Systems. Retrieved online http://www.cdrsys.ca/prone-head.html. Print date Jan. 9, 2018, 2 pages.
Prone Head Holder, Uni-frame. Civco Radiotherapy. Retrieved online http://civcort.com/ro/head-neck/uniframe-baseplates/Uni-frame-Prone-Head-Holder.htm. Print date Jan. 9, 2018, 2 pages.
Civco Solutions Guide vol. 3.0. Civco Radiotherapy. 2016, 116 pages.

* cited by examiner

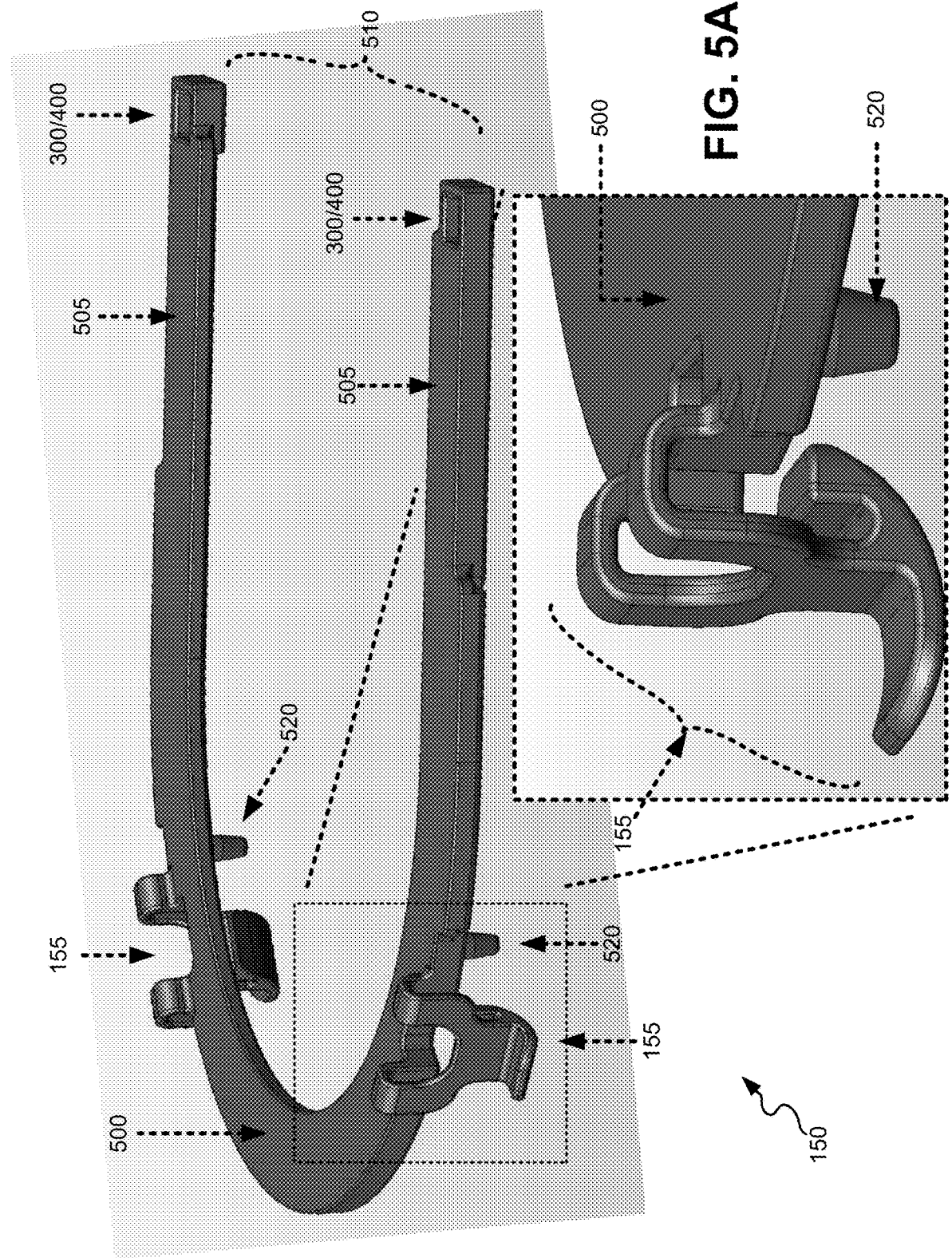

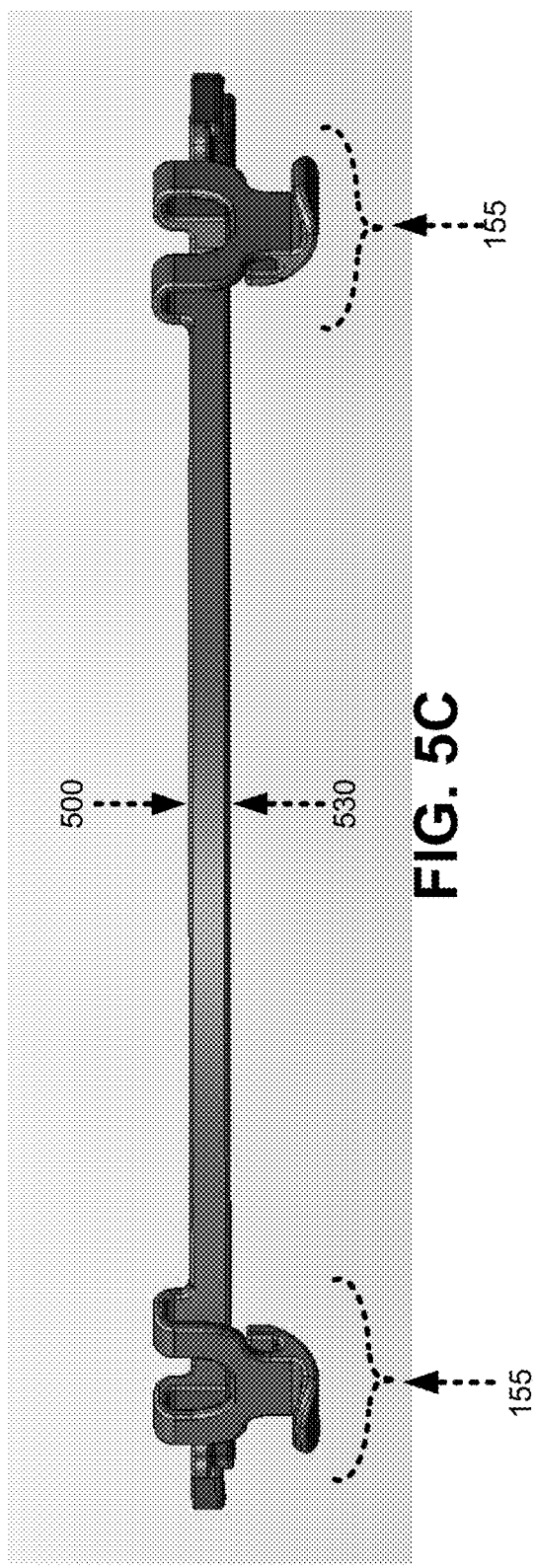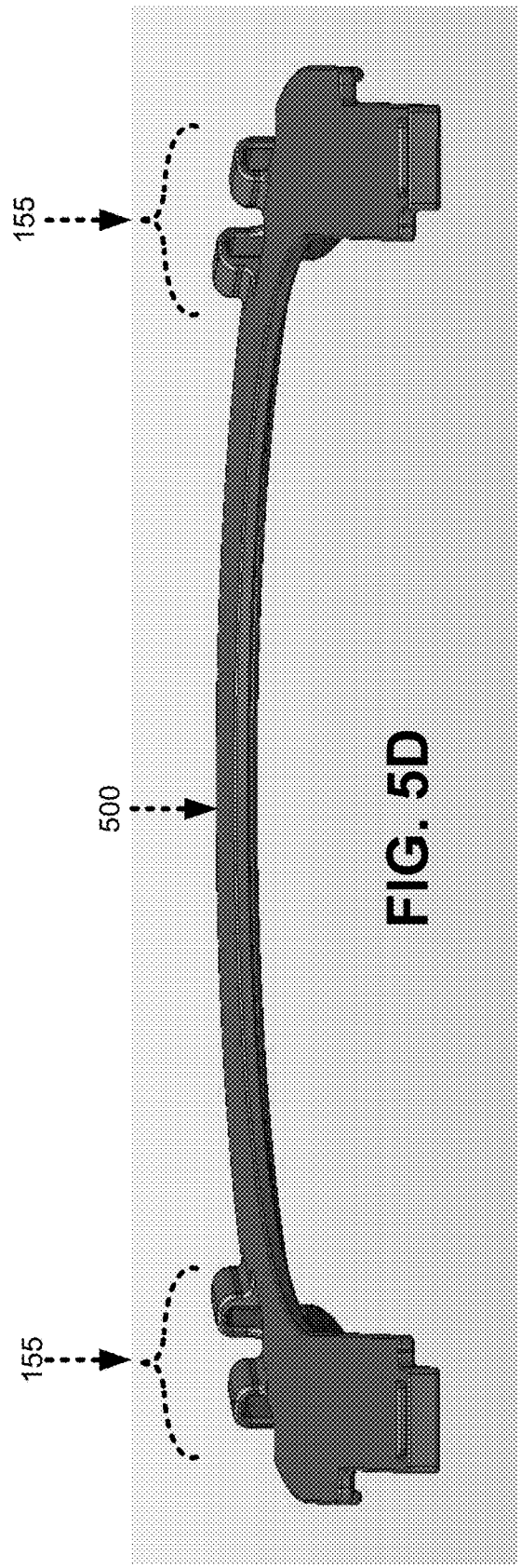

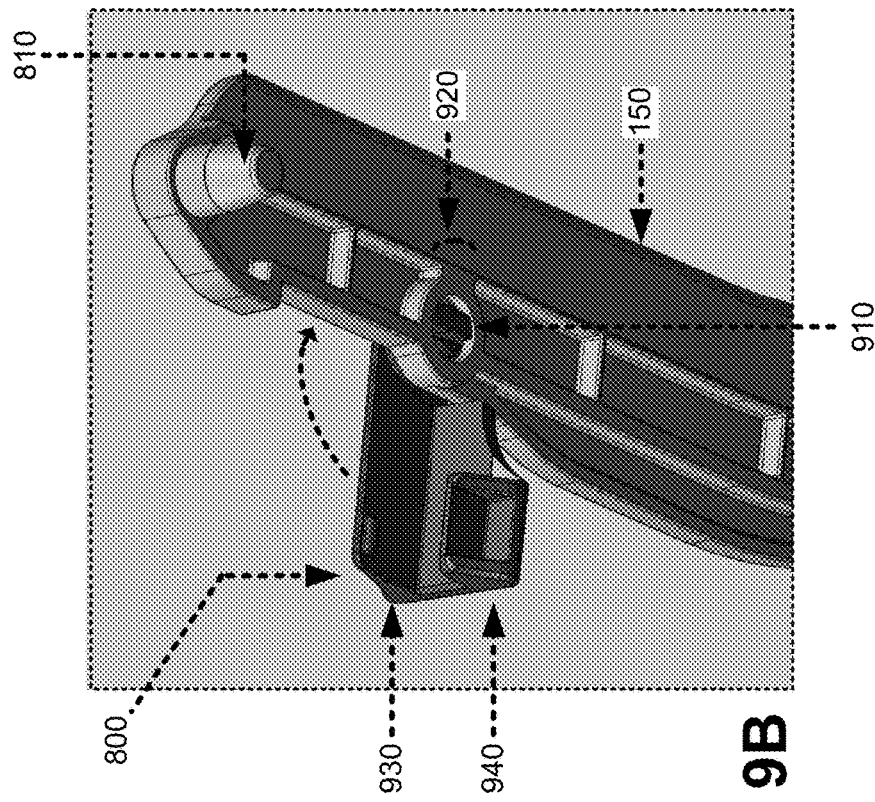
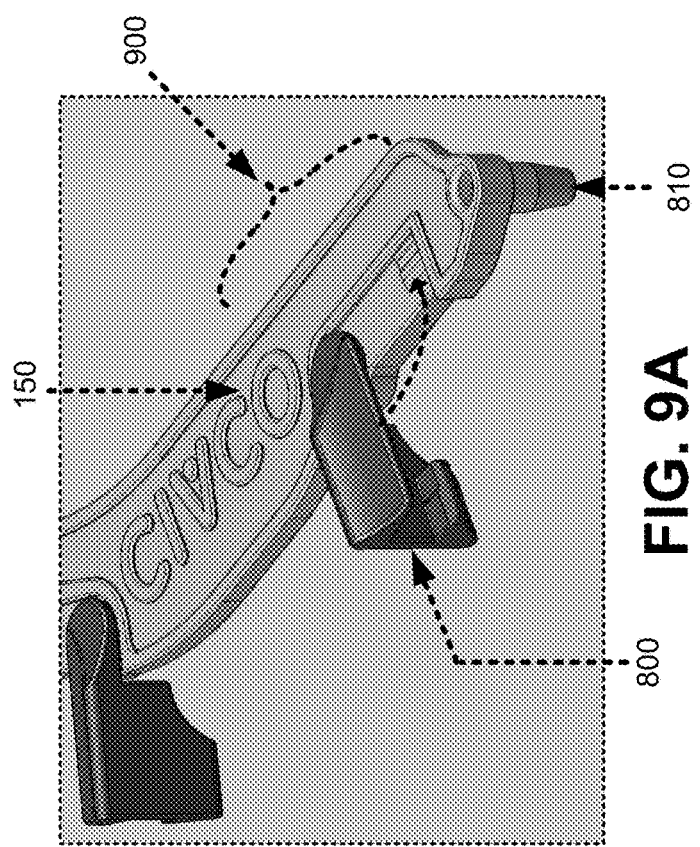
FIG. 9A
FIG. 9B

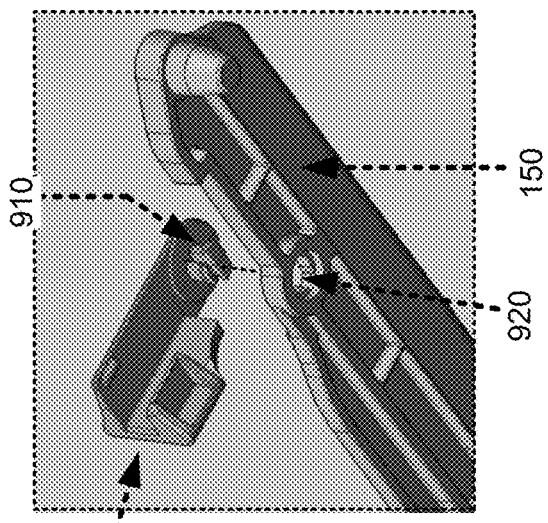
FIG. 9D
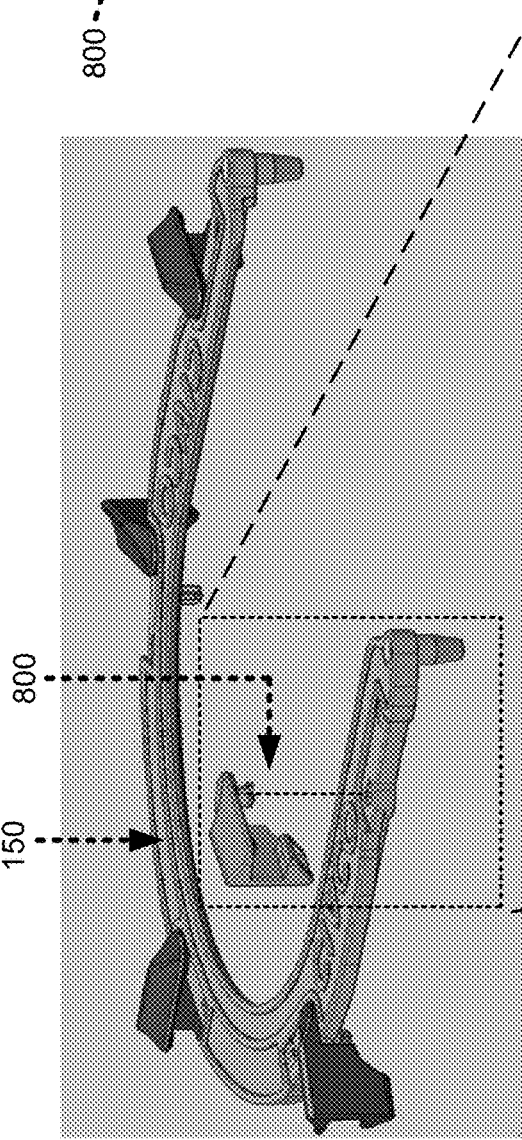
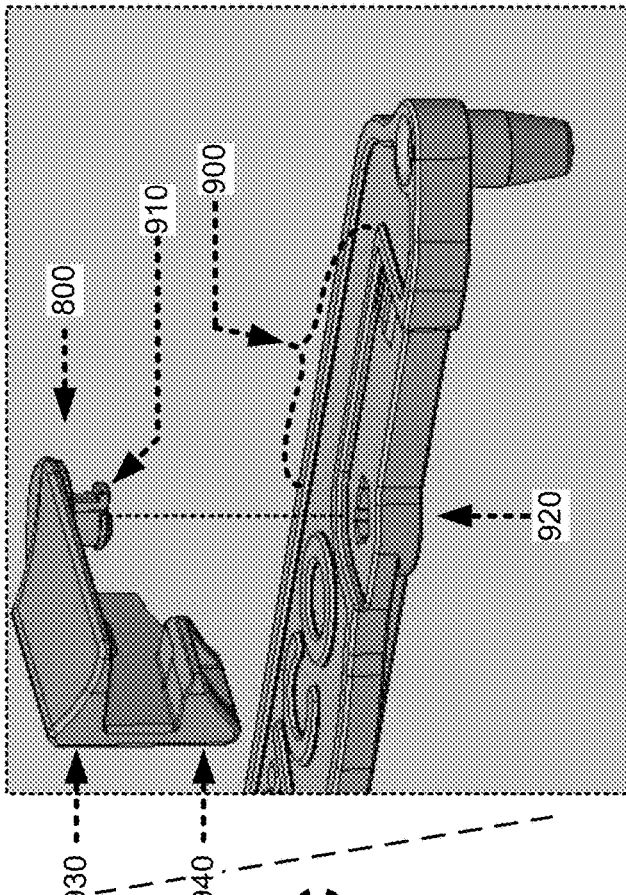
FIG. 9C

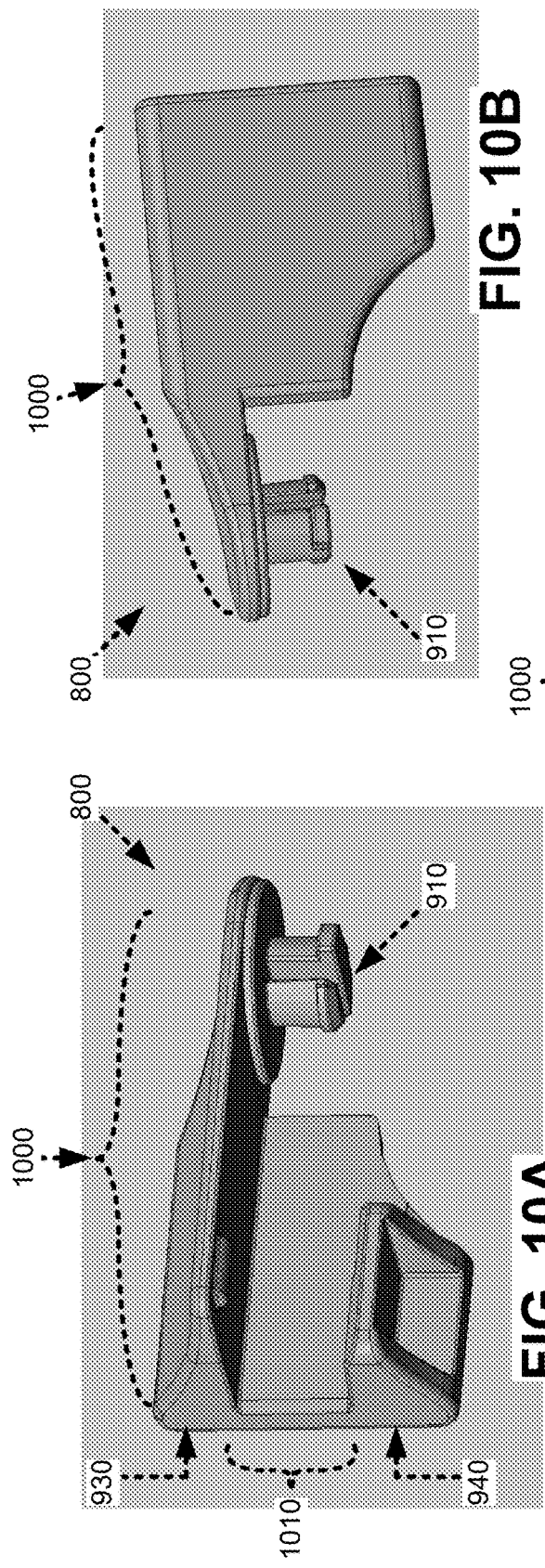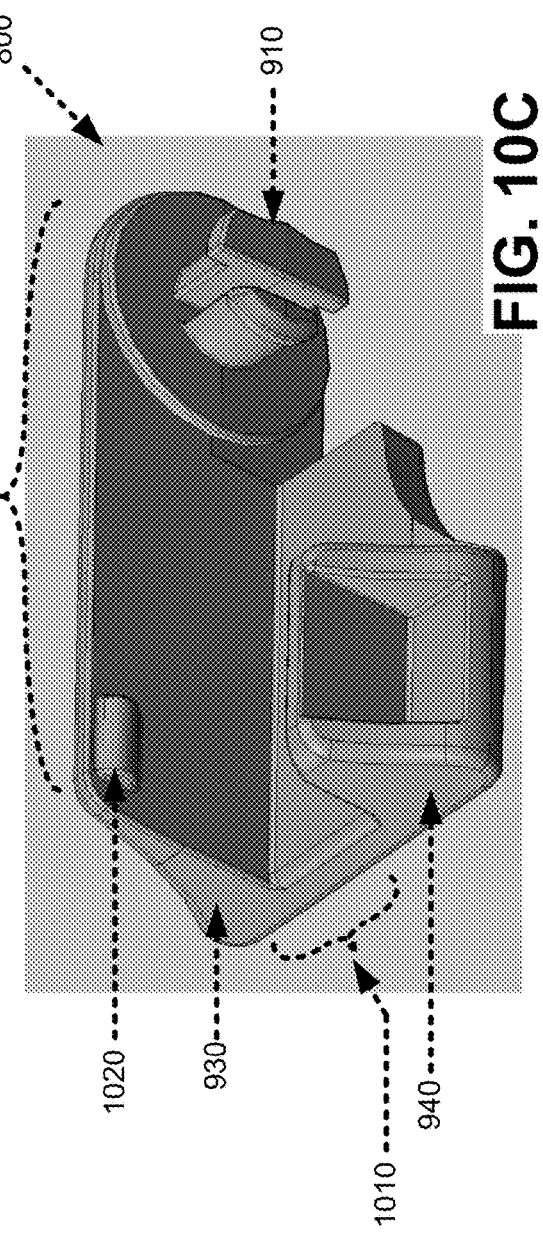

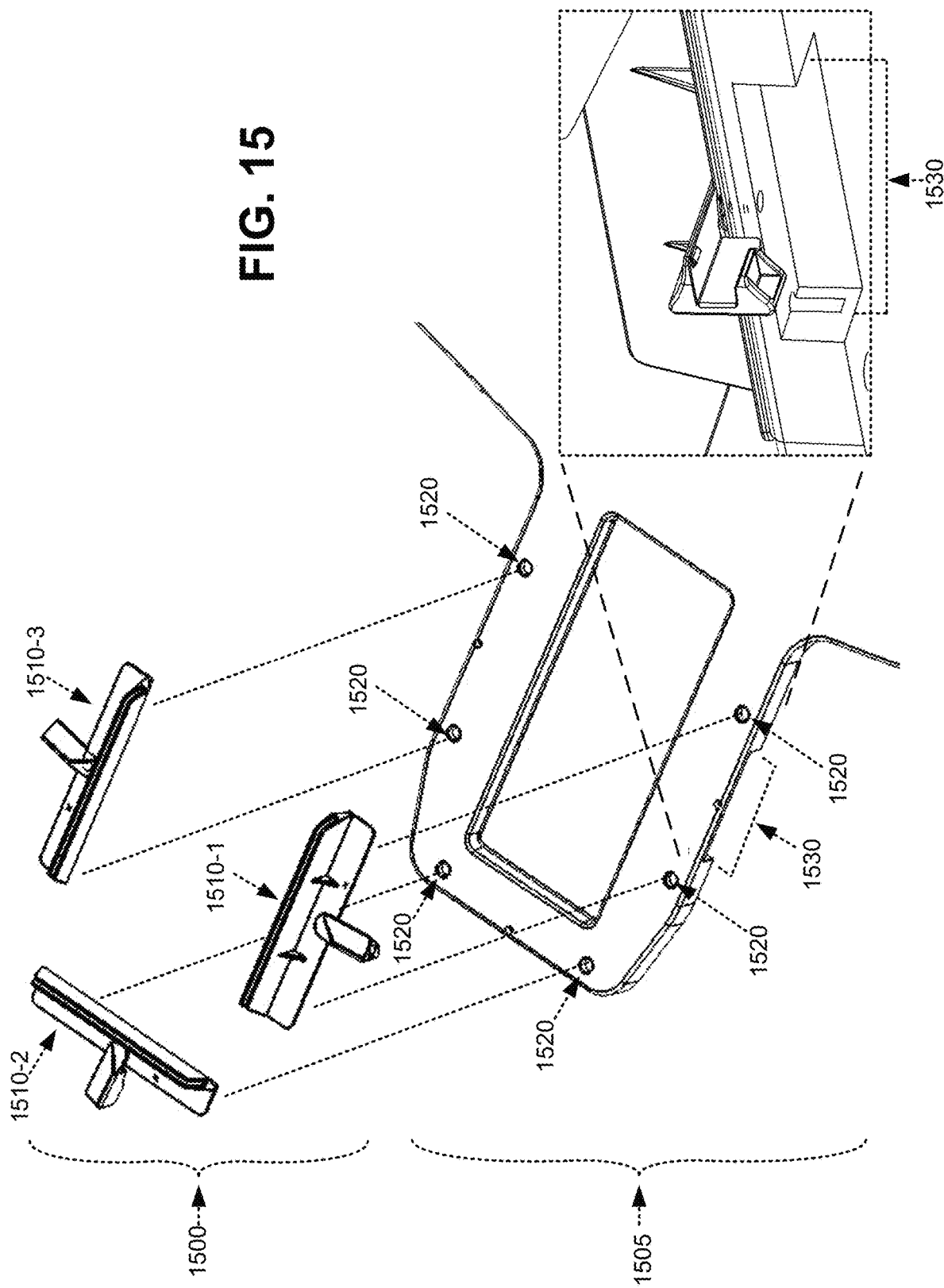

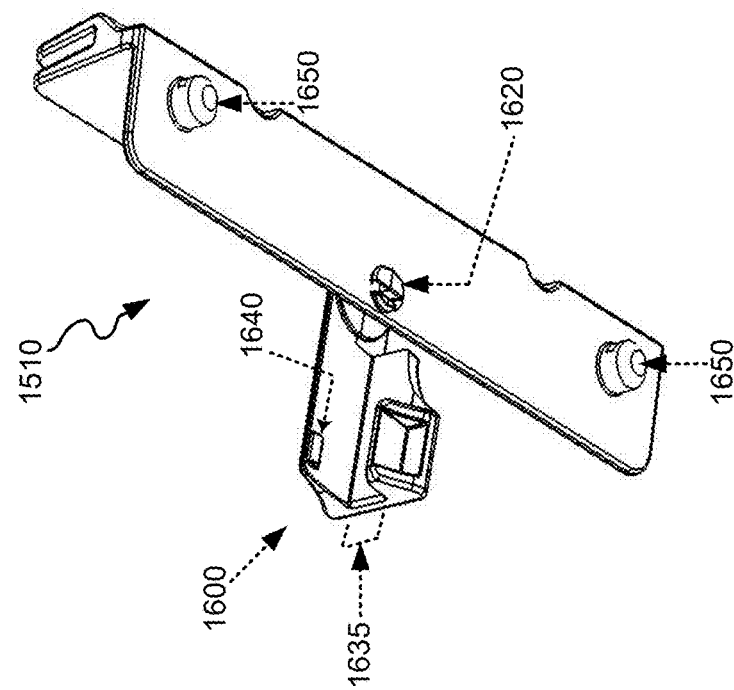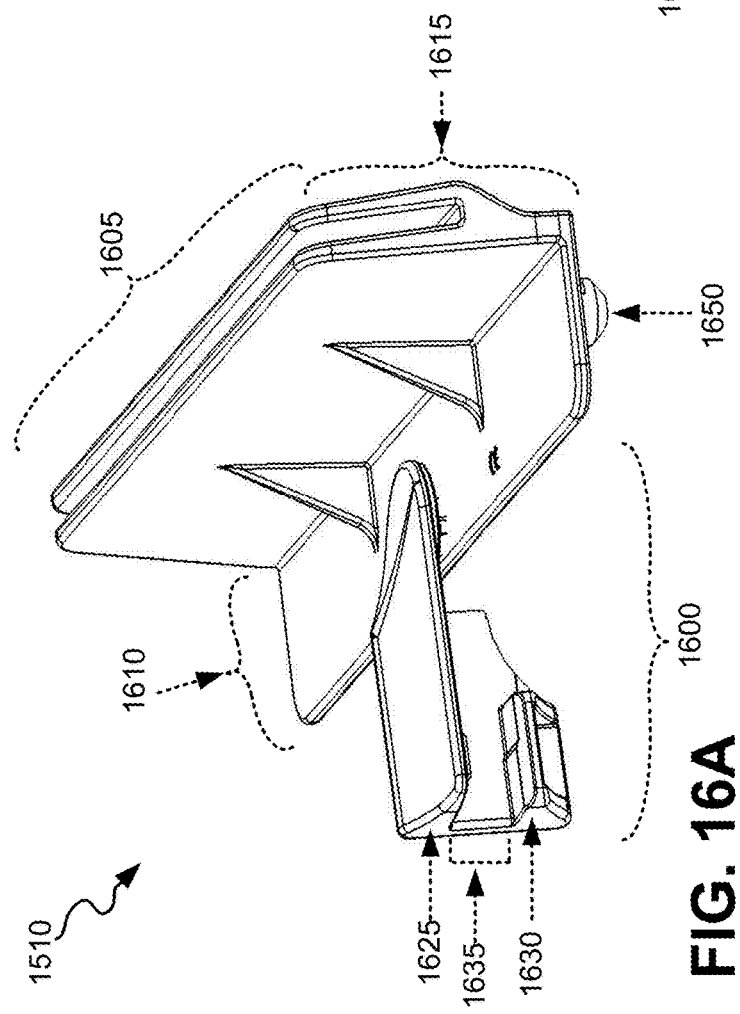

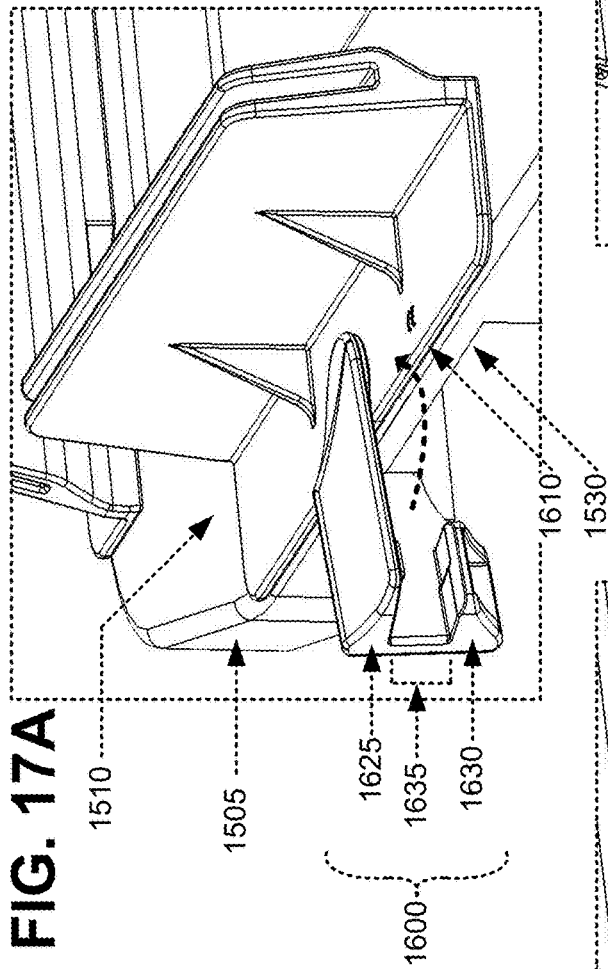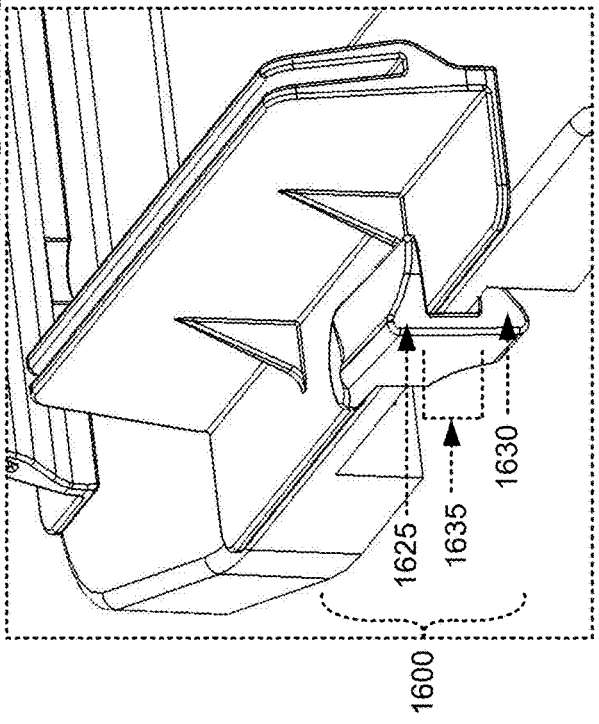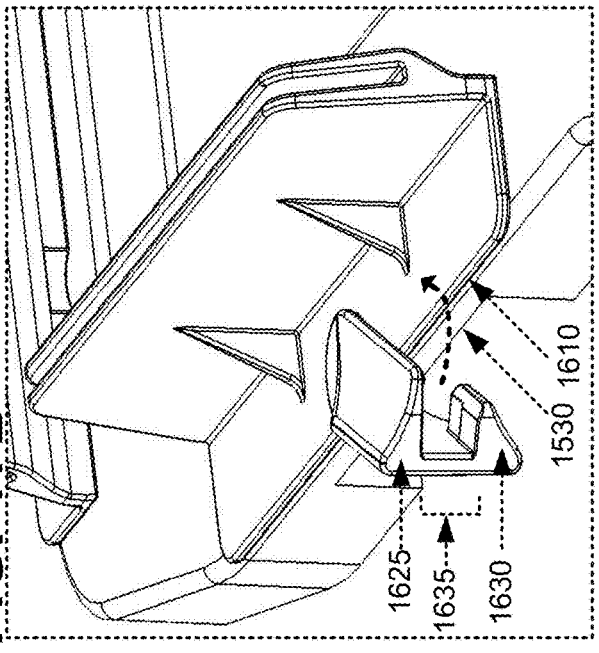

EASY ON/EASY OFF CLIPS OR CLAMPS FOR MOUNTING MASK TO BODY PART FIXATION DEVICE

RELATED APPLICATION

This application further claims priority under 35 U.S.C. § 119, based on U.S. Provisional Application No. 62/648,011, filed Mar. 26, 2018, the disclosure of which is hereby incorporated by reference herein.

BACKGROUND

Certain types of medical treatments require that a portion of a human body be held in a same position to facilitate performance of the medical treatment upon that portion of the body. For example, when brain cancer patients undergo radiation treatment, their heads must be maintained in a precise, repeatable location for the treatment such that the underlying position of the brain tumor is fixed in space for the duration of the radiation treatment or treatments. Various different techniques have been used in the field of radiation oncology for holding body parts in a fixed position.

BRIEF DESCRIPTION OF THE DRAWINGS

FIGS. 5A-5E depict side, front, rear, top, and bottom views of the mask frame of FIGS. 1A and 1B in an embodiment in which the mask frame has a U-shape;

FIGS. 9A and 9B depict further details of the configuration of, and operation of, a pivoting clamp of the exemplary embodiment of FIG. 8;

FIGS. 9C and 9D depict additional details of the mounting of a pivoting clamp to the mask frame of the exemplary embodiment of FIG. 8;

FIGS. 10A-10C depict a physical configuration of an exemplary implementation of the pivoting clamps of FIG. 8;

FIG. 15 depicts a further exemplary embodiment in which the body part immobilization device includes a body part immobilization table and a multi-piece mask frame having clips or clamps;

FIGS. 16A and 16B depict different views of a single frame piece of the multi-piece mask frame of FIG. 15;

FIGS. 17A, 17B, and 17C depict an exemplary sequence associated with using a pivoting clamp to fasten a single frame piece of the multi-piece mask frame to a body part immobilization table;

DETAILED DESCRIPTION OF THE PREFERRED EMBODIMENTS

Figure 1A:
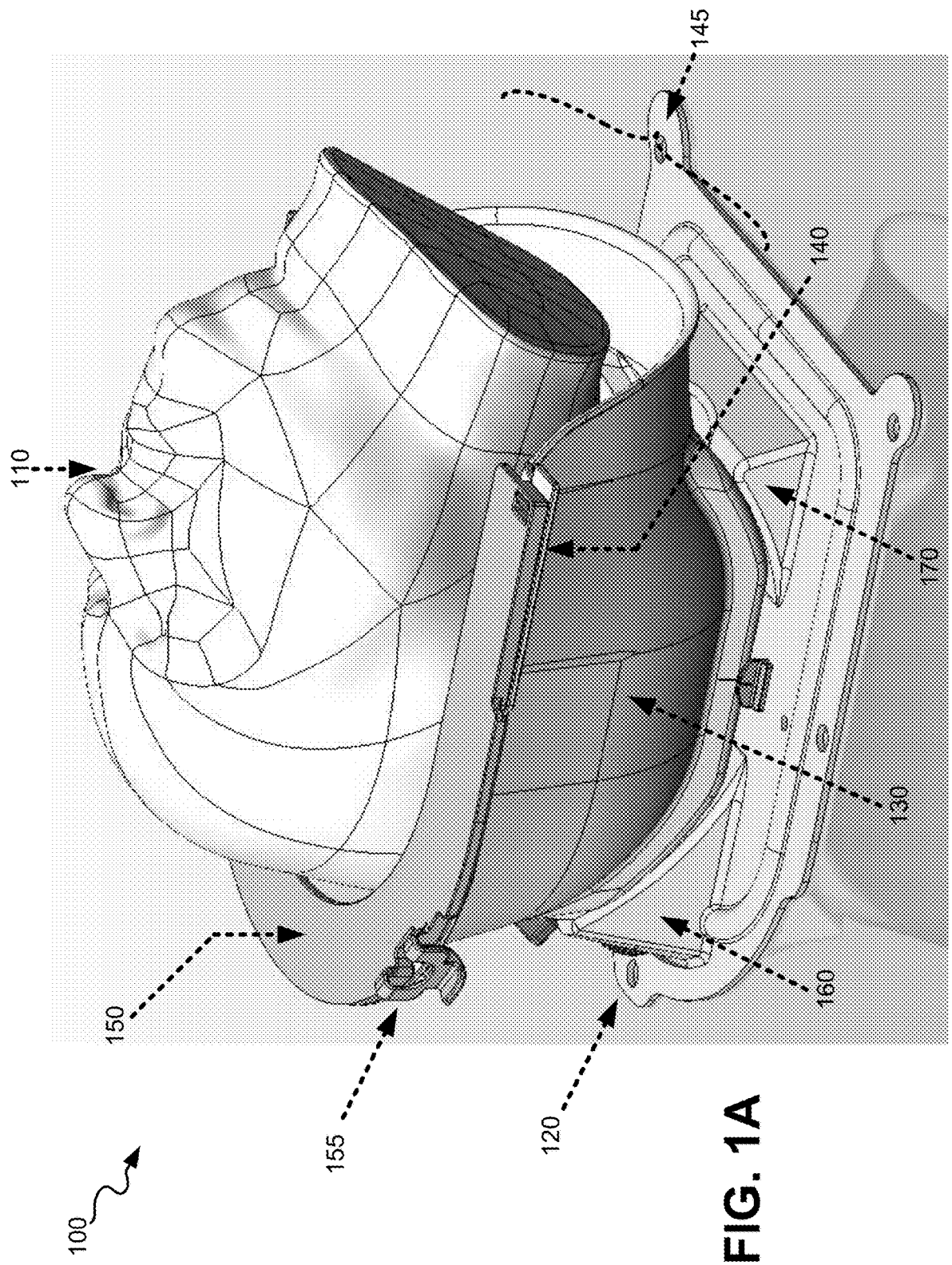
FIGS. 1A and 1B depict views of an exemplary embodiment in which a body part immobilization device is configured to immobilize a head of a patient.

The following detailed description refers to the accompanying drawings. The same reference numbers in different drawings may identify the same or similar elements. The following detailed description does not limit the invention.

A technique, in the field of radiation oncology, for holding body parts in a fixed position uses heat-formable structures that include a sheet of retention material that is stretched over the body part of the patient. For example, for performing radiation treatment of a brain tumor, the heat-formable structure includes a mask having a sheet of retention material that is stretched over the patient's face. To form the mask over the patient's face, a hot water bath or oven may be first used to heat the material of the heat-formable structure such that the sheet of material becomes pliable and deformable. The heat-formable mask is then stretched over the patient's face, and the mask is allowed to cool and harden, permanently forming the mask to the shape of the face of the patient. As an example, a mask having a sheet of thermoplastic retention material, after heating, may be stretched over a patient's face, and then allowed to cool. Upon cooling, the mask, formed to the patient's face, creates a structure that can be used to hold the patient's head in a fixed position during radiation treatments. After the sheet of thermoplastic retention material of the mask is stretched over the body part of the patient, a frame portion of the mask is attached to a patient support table, or other structure, using an attachment mechanism(s). Existing body part fixation devices have fairly complicated mechanisms for fastening the frame portion of the mask to the patient support table. Such complicated mechanisms can make fastening the mask to the patient support table to fix the position of the underlying body part, or unfastening the mask from the patient support table once the medical test or treatment has completed, a cumbersome process.

Exemplary embodiments described herein relate to improvements over existing attachment mechanisms for attaching the frame of a body part mask to a body part immobilization device. Embodiments described herein use easy on/easy off clips, connected either to the mask frame, or to an upper portion (e.g., upper flange) of a body part immobilization device, for quickly and easily mounting, and fastening, the body part mask at a fixed position on the body part immobilization device. Further embodiments described herein use easy on/easy off pivoting clamps connected to the mask frame for quickly and easily mounting/docking, and fastening, the body part mask at a fixed position on the body part immobilization device.

The body part immobilization device, in one implementation described herein, includes a deep shell frame that receives and positions a body part, where the shell has an inner shape that conforms to the shape of the body part being immobilized (e.g., a patient's head). The shell frame additionally may contain a cushion (e.g., head cushion) that is customized to fit the body part of the patient. For example, when the body part is a patient head, the depth of the shell frame enables the customized cushion to surround the head up to a mid-point of the head, providing a large contact surface area that permits a substantial area of support for the head. The shell frame may additionally include an upper flange that permits "easy on/easy off" attachment of the mask frame to the flange. Docking of the mask frame at the upper flange of the shell frame eliminates the need to stretch the thermoplastic material of the mask all the way down to the support table surface, thereby, enhancing the thickness and rigidity of the sheet of mask material.

The body part immobilization device, in another implementation described herein, includes a body part immobilization table, upon which a body part is positioned, and to which a mask frame, such as a multi-piece mask frame, attaches using clips or clamps after form fitting the material of the mask to the body part being immobilized. The body part immobilization table may be substantially flat, and the multi-piece mask frame may include two or more mask frame pieces to which the body part immobilizing material (e.g., thermoplastic material) of the mask attaches. The two or more mask frame pieces may each include at least one clip or clamp for attaching the mask frame piece to the underlying body part immobilization table.

A "mask," as referred to herein, includes any structure having a material (e.g., a thermoplastic material) that can be pulled over any body part of a patient to form fit the material to the body part. In some embodiments, a "mask" enables the body part to be immobilized and held in a specific position using a fastening mechanism(s) that may, or may not, be a component of the mask. Thus, a "mask," as used herein, does not refer solely to a structure for placement over a patient's face or head, but includes any type of structure for placement over any body part, or any portion of the body, of a patient (e.g., a structure that pulls over a pelvis of a patient).

Figure 1B:
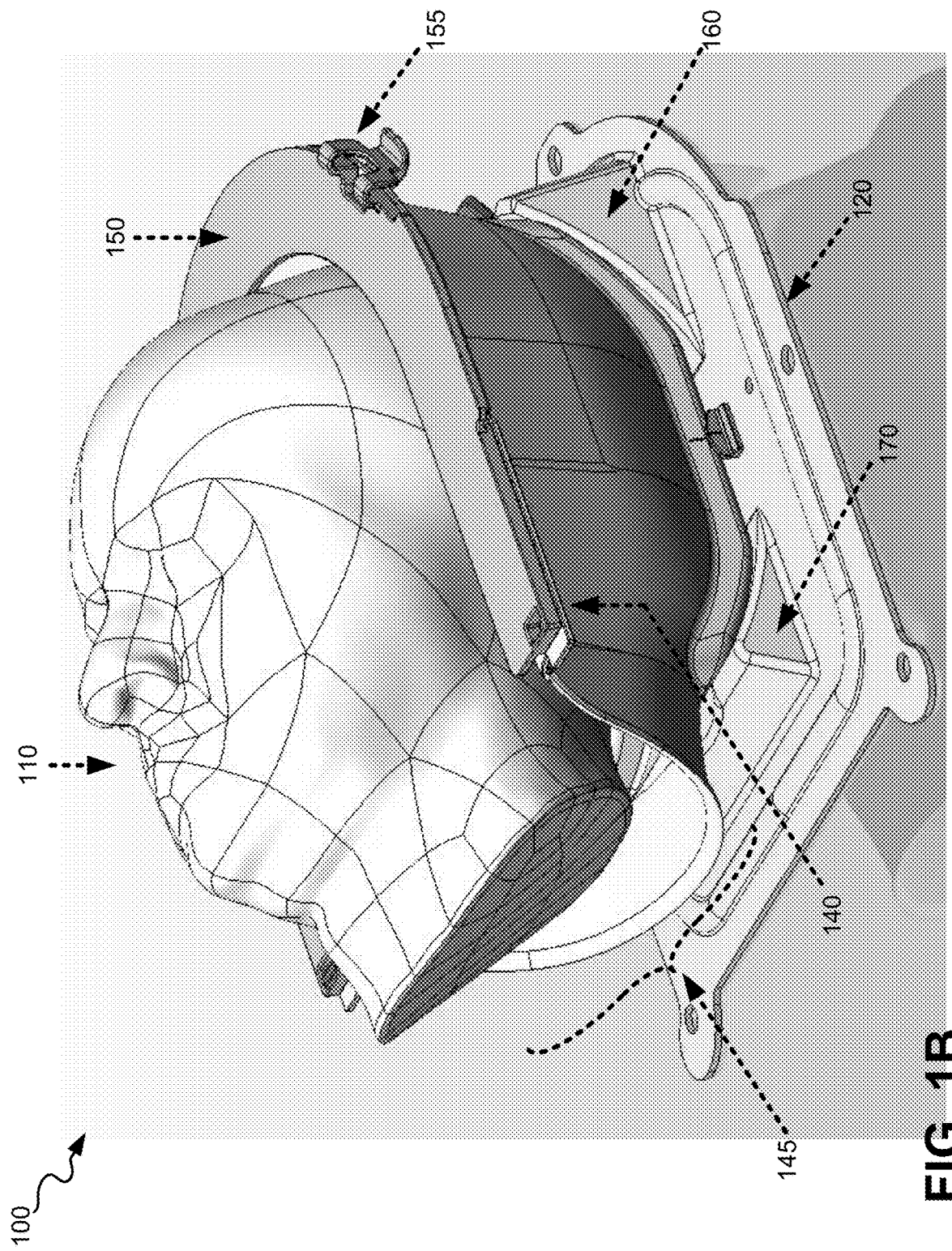

FIGS. 1A and 1B depict views of an exemplary embodiment in which a body part immobilization device 100 is configured to immobilize a head 110 of a patient. As shown in FIG. 1A, immobilization device 100 includes a support base 120 and a shell frame 130. Shell frame 130, in the embodiment shown in FIGS. 1A and 1B, may include an approximate half shell structure having an inner surface that is configured to conform to a back of the patient's head and neck. The half shell structure of shell frame 130 has a shape that approximates half of a three dimensional spheroid, where the half roughly transects a vertical center of the spheroid. Shell frame 130 may include a neck cutout 145 in one side of the shell frame 130 that is configured to conform to the neck of the patient and enables, when the patient's head 110 is laid within shell frame 130, the neck to extend out of the interior of shell frame 130. As shown in FIGS. 1A and 1B (and also in FIG. 2A), an upper edge of shell frame 130 includes a flange 140 that extends around a perimeter of the upper edge of the shell frame 130. The flange 140 extends approximately ½ to ¾ of an inch out from the upper edge of shell frame 130. Other types of shell frames, or other types of underlying structures, having a different physical configuration than shell frame 130 shown in FIGS. 1A and 1B, may alternatively be used within body part immobilization device 100. Mask frame 150 may, therefore, mount to (i.e., clip onto, or unclip from) differently structured shell frames, or to different types of underlying structures, than shell frame 130 shown in FIGS. 1A and 1B.

As shown in FIGS. 1A and 1B, to fix the position of the patient's head 110 within shell frame 130, a frame 150 of a mask may be placed in position upon the upper flange 140 of shell frame 130 to mount the mask to shell frame 130. Multiple clips 155 may be disposed around an outer perimeter of mask frame 150 and permit mask frame 150 to be quickly and easily fastened or unfastened to the upper flange 140 of shell frame 130. As shown in FIGS. 1A and 1B, clips 155 may be integral to mask frame 150.

In the embodiment depicted in FIGS. 1A and 1B, support base 120 includes a first pitch shell ramp 160 and a second pitch shell ramp 170 that are disposed on support base 120 opposite one another and at a sufficient distance apart to enable the lower surface of shell frame 130 to rest upon support base 120 between the two pitch shell ramps. Pitch shell ramp 160 and pitch shell ramp 170 include sloping ramps that extend downwards towards a center of support base 120. Other types of support bases, having a different physical configuration than support base 120 shown in FIGS. 1A and 1B, may alternatively be used with shell frame 130 within body part immobilization device 100. Shell frame 130 and support base 120 may be formed from various types of materials, including metal, plastic, carbon fiber, or a composite material. Shell frame 130 and support base 120 may each be formed from a same type of material, or a different type of material. For example, support base 120 may be formed from metal, and shell frame 130 may be formed from a composite material.

Figure 2A:
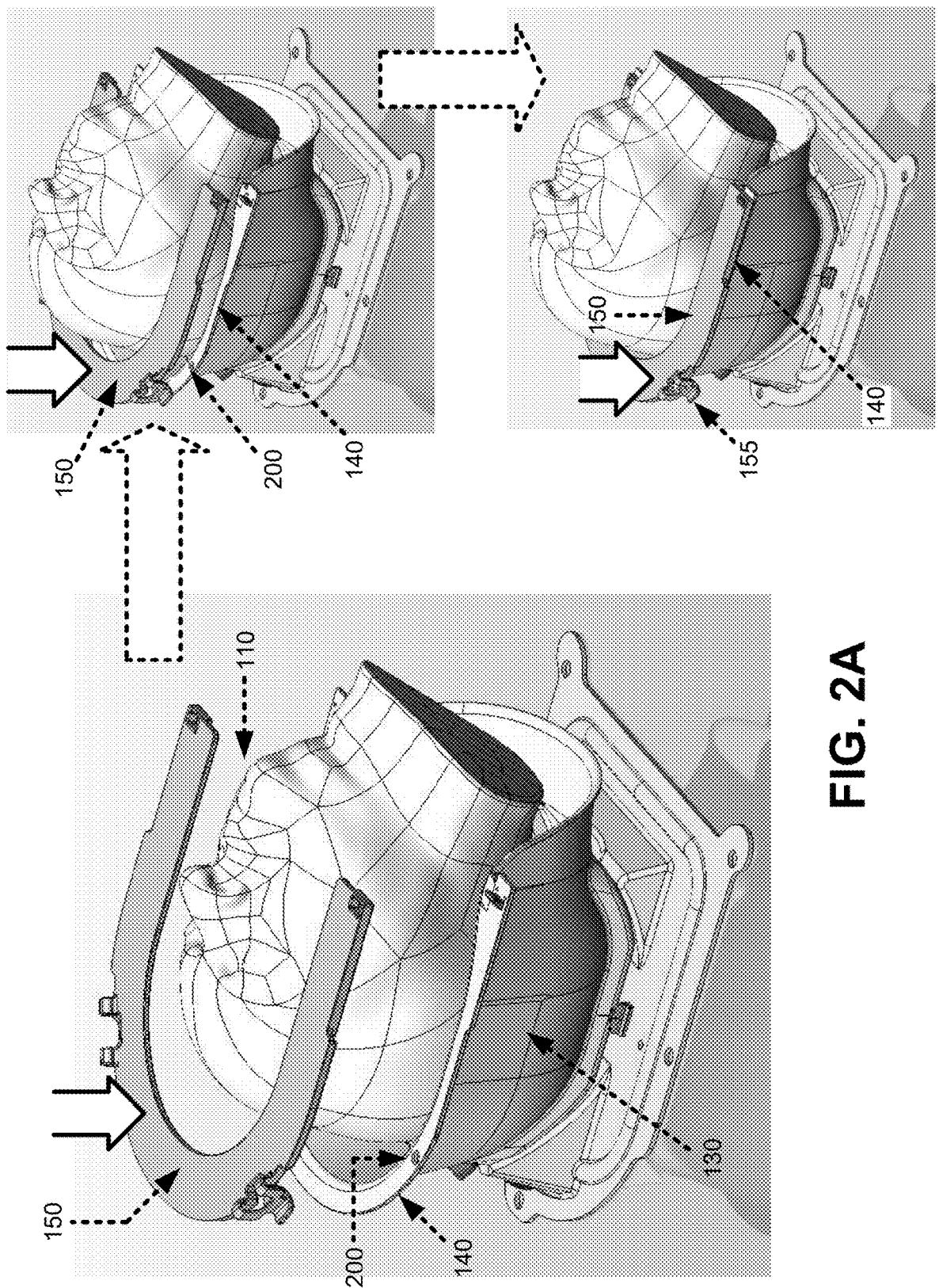
FIG. 2A depicts further details of the mounting of a mask frame onto a flange of the shell frame of FIGS. 1A and 1B.

FIG. 2A depicts further details of the mounting of mask frame 150 onto upper flange 140 of shell frame 130. As shown, mask frame 150, including a sheet of stretchable mask material (not shown in FIG. 2A), may be placed over the patient's head 110, and moved downwards until the bottom of mask frame 150 contacts the upper flange 140 of shell frame 130. Once mask frame 150 is mounted upon the upper flange 140 of shell frame 130, the clips 155 of frame 150 may be engaged to clip onto the upper flange 140 such that mask frame 150 is fastened to shell frame 130. Mounting mask frame 150 to shell frame 130 causes the sheet of stretchable mask material (not shown in FIG. 2A) to stretch over the face of the patient such that the patient's head 110 is held in position within shell frame 130.

FIG. 2A additionally depicts exemplary details of upper flange 140 of shell frame 130. As shown, an upper surface of flange 140 includes multiple registration holes 200 (only one is viewable in FIG. 2A) for docking mask frame 150 to shell frame 130. Mask frame 150 may further include multiple pins (not shown) on an underside of the frame 150, that line up with, and can be inserted into, the registration holes 200. When docking mask frame 150 to shell frame 130, the registration holes ensure the proper positioning of mask frame 150 relative to flange 140 of shell frame 130.

Figure 2B:
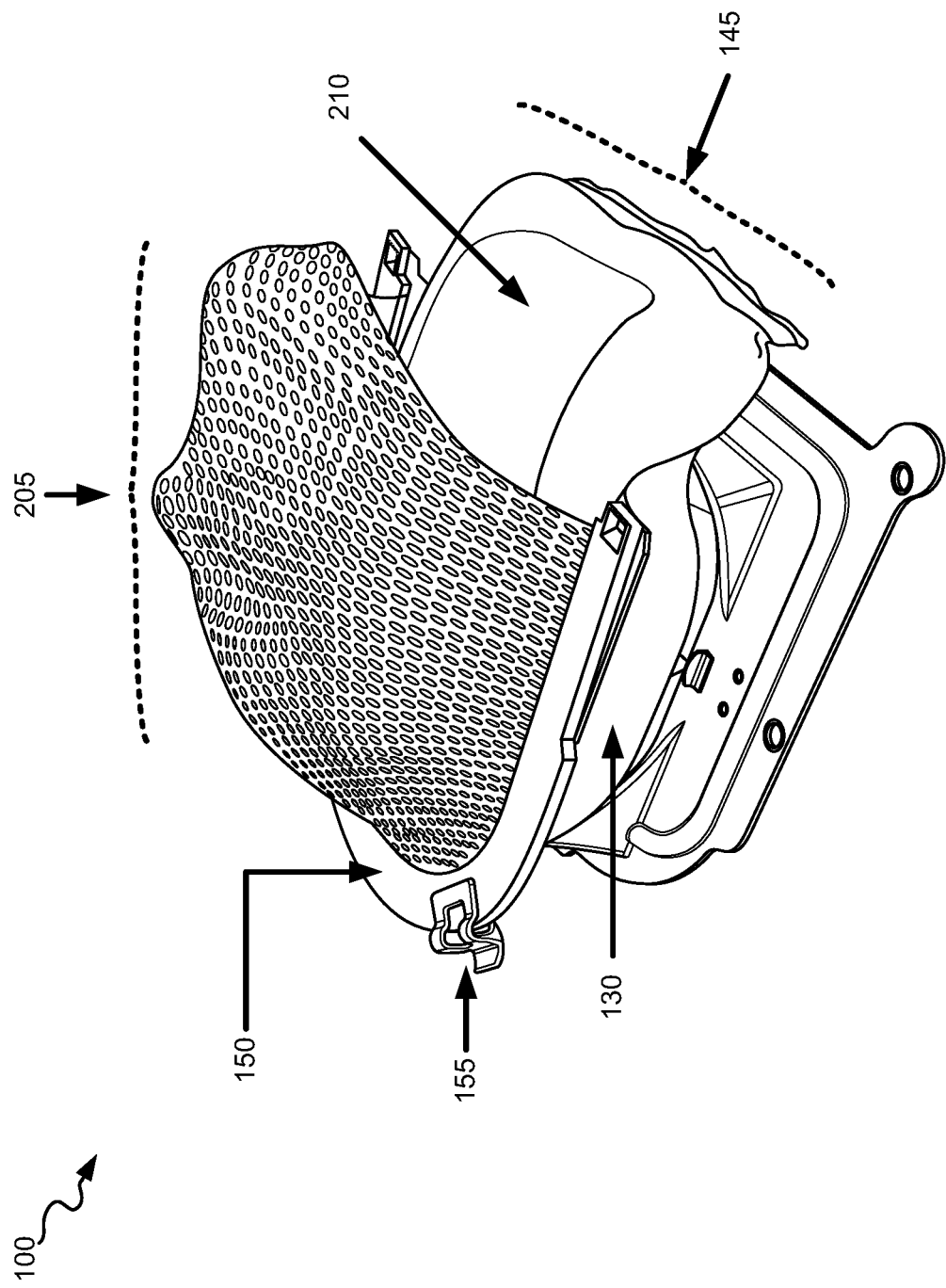
FIG. 2B includes a pictorial representation of the body part immobilization device of FIGS. 1A and 1B that explicitly shows the mask attached within the mask frame.

FIG. 2B includes a pictorial representation of body part immobilization device 100 that explicitly shows the sheet of mask material 205 (omitted from the views in FIGS. 1A, 1B, and 2A) attached within mask frame 150. As can be seen in FIG. 2B, a head cushion 210 may be placed within shell frame 130 to cushion the patient's head 110 (not shown) against shell frame 130. Given the deep nature of shell frame 130, the head cushion 210 surrounds the head 110 (not shown) up to a top of shell frame 130, thus, providing a large contact surface area and good support for the head 110. With the head 110 supported upon head cushion 210, mask material 205 and mask frame 150 may be docked to shell frame 130 using clips 155, as described further below. In the exemplary embodiment depicted in FIG. 2B, multiple spring clips 155 are used to fasten mask frame 150 to shell frame 130. The multiple spring clips 155 may be integral to the mask frame 150, may be integral to the shell frame 130, or may be separate and detached items that can be used to fasten mask frame 150 to shell frame 130 when mask frame 150 is docked with shell frame 130.

Figure 3:
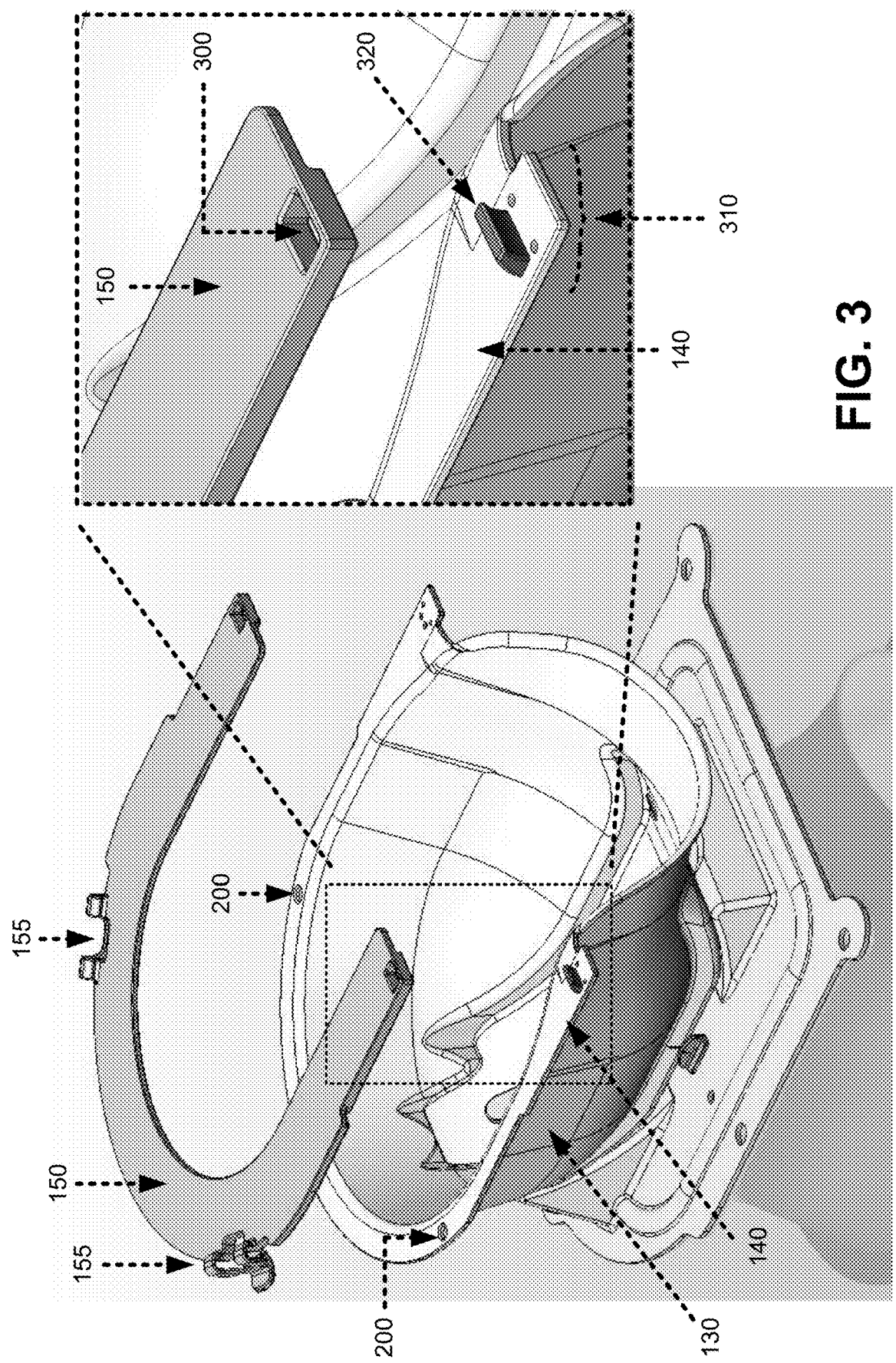
FIG. 3 depicts exemplary fastening mechanisms used to fasten the mask frame to the shell frame according to a first exemplary embodiment.

FIG. 3 depicts exemplary fastening mechanisms used to fasten mask frame 150 to shell frame 130 according to a first exemplary embodiment. The fastening mechanisms, in the exemplary embodiment depicted in FIG. 3, includes spring clips 155 and retention tabs. As shown in the breakout view of FIG. 3, each arm of mask frame 150 terminates in a retention hole 300 that extends from a lower surface of mask frame 150 through to an upper surface of mask frame 150. A corresponding retention tab 320, mounted upon upper flange 140 at a terminating position 310, may, when mask frame 150 is lowered such that retention tab 320 extends into retention hole 300, hold the arm of mask frame 150 in position upon upper flange 140 of shell frame 130. A retention tab 320 may be mounted upon upper flange 140 at the terminating position 310 at each side of neck cutout 145 of shell frame 130. In this exemplary embodiment of FIG. 3, retention tabs 320 may be removably mounted upon upper flange 140 of shell frame 130 such that if retention tabs 320 are damaged, or worn out, from use, retention tabs 320 may be replaced with new retention tabs 320.

Figure 4:
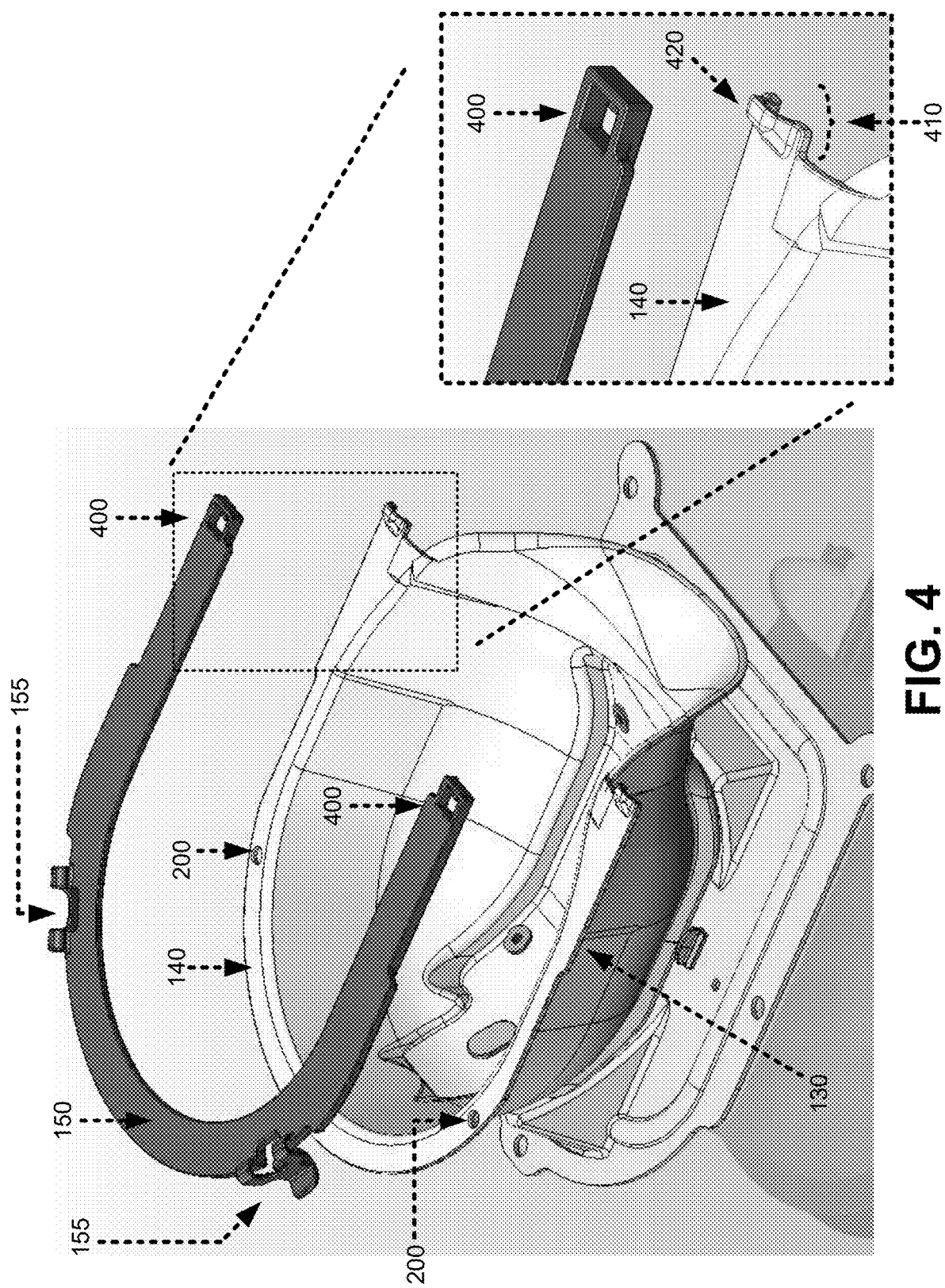
FIG. 4 depicts exemplary fastening mechanisms used to fasten the mask frame to the shell frame according to a second exemplary embodiment.

FIG. 4 depicts exemplary fastening mechanisms used to fasten mask frame 150 to shell frame 130 according to a second exemplary embodiment. The fastening mechanisms, in the exemplary embodiment depicted in FIG. 4, includes spring clips 155 and projection members. As shown in the breakout view of FIG. 4, each arm of mask frame 150 terminates in a retention hole 400 that extends from a lower surface of mask frame 150 through to an upper surface of mask frame 150. A corresponding projection member 420, formed upon upper flange 140 at a terminating position 420, may, when mask frame 150 is lowered such that projection member 420 extends into retention hole 400, hold the arm of mask frame 150 in position upon upper flange 140 of shell frame 130. A projection member 420 may be located upon upper flange 140 at the terminating position 420 at each side of neck cutout 145 of shell frame 130. In this exemplary embodiment of FIG. 4, projection members 420 may be formed in upper flange 140 at the time shell frame 130 is formed (i.e., comprises an integral member of flange 140).

Figure 5B:
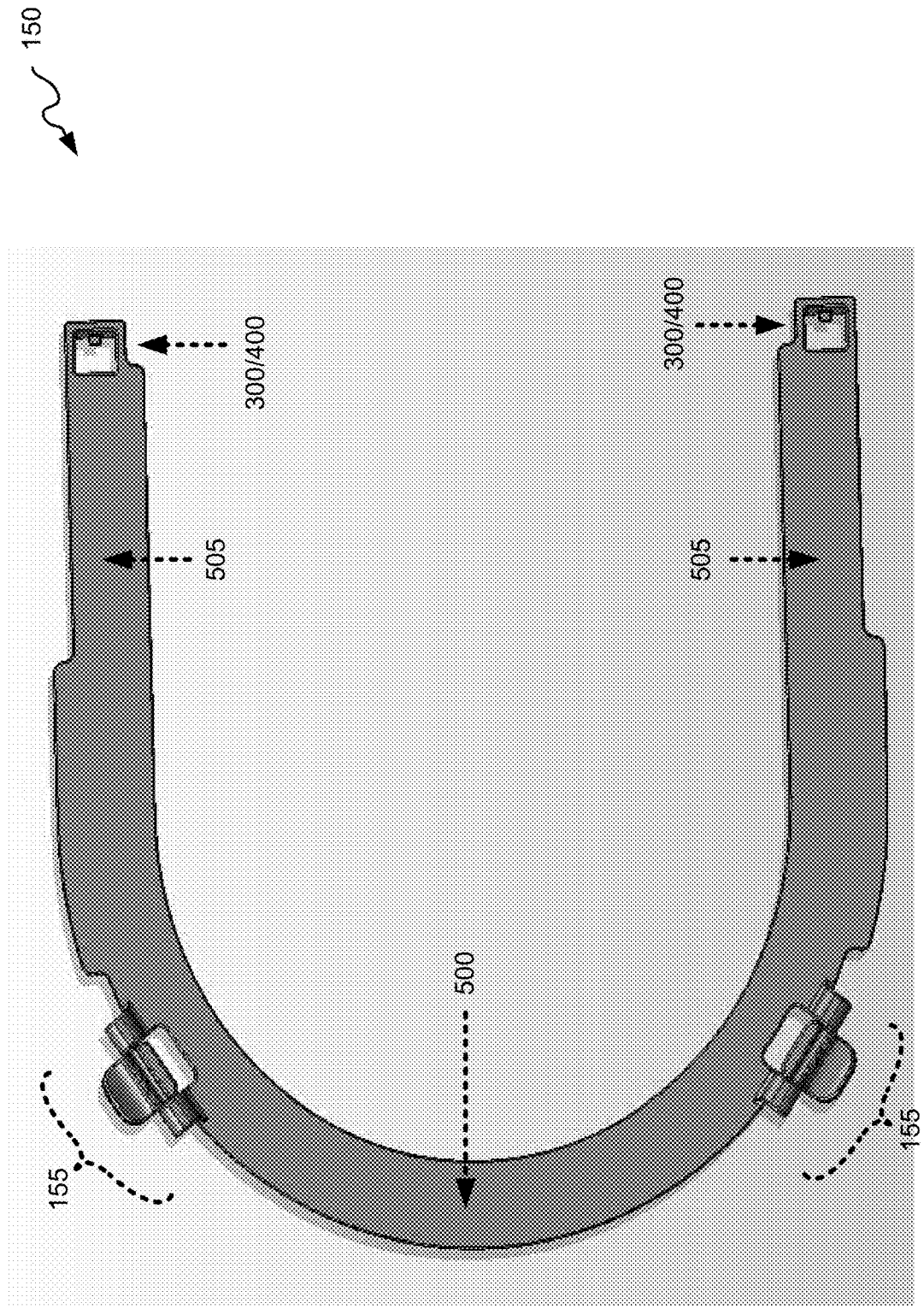

FIGS. 5A-5E depict side, front, rear, top, and bottom views, respectively, of mask frame 150 in an embodiment in which mask frame 150 has a U-shape. The embodiment shown in FIGS. 5A-5E includes two spring clips 155. In other embodiments, more spring clips 155 (e.g., 3 or more) or fewer spring clips 155 (e.g., a single spring clip) may alternatively be used. As shown in the side view of FIG. 5A, the U-shape of mask frame 150 includes two arms 505 that encompass an open area 510 within the U-shape of mask frame 150. The two arms 505 of mask frame 150 each terminate with a retention hole 300/400. Multiple spring clips 155 connect or attach to an upper surface 500 of mask frame 150 at spaced part locations along an outer perimeter of the upper surface 500. In the embodiment of FIGS. 5A-5E, mask frame 150 has two spring clips 155 that are located at opposing locations upon each arm 505. In other embodiments, mask frame 150 may include fewer or more spring clips 155 spaced along the perimeter of upper surface 500. The break out view of FIG. 5A further shows details of a spring clip 155 and its connection to the upper surface 500 of mask frame 150. FIG. 5A further depicts registration pins 520 that may be used to align mask frame 150 with corresponding registration holes 200 within the upper flange 140 (not shown in FIG. 5A) of shell frame 130.

Figure 5E:
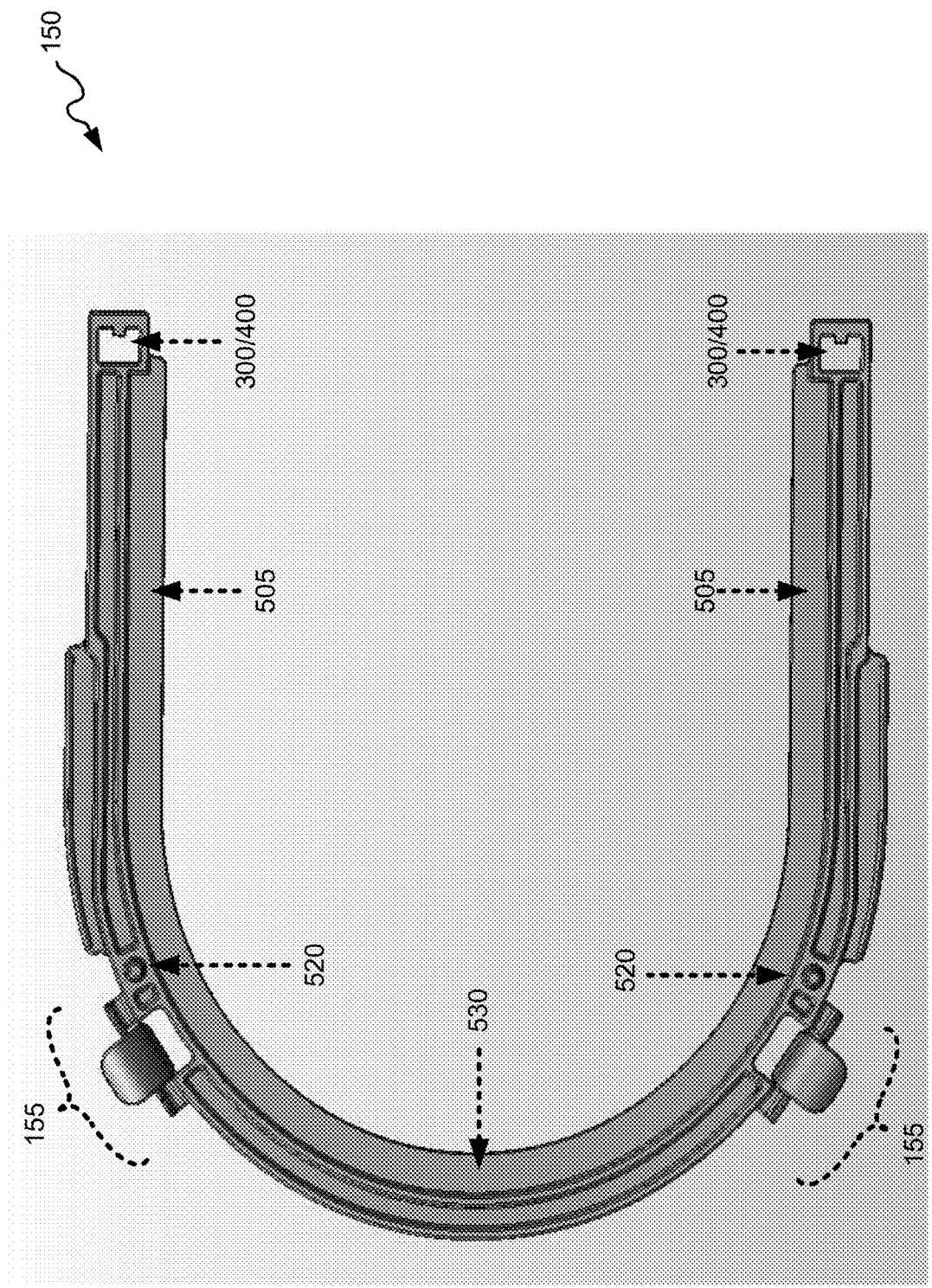

FIG. 5B depicts a top view of mask frame 150 in which the locations of retention holes 300/400 at the termination of each arm 505 upon the upper surface 500 are shown. FIG. 5B further shows a top view of spring clips 155 and their connection to the outer perimeter of the upper surface 500 of mask frame 150. FIGS. 5C and 5D illustrate front and rear views of mask frame 150. A lower surface 530 of mask frame 150 can be seen in the front view of FIG. 5C. FIG. 5E depicts a bottom view of mask frame 150 in which the locations of retention holes 300/400 at the termination of each arm 505, and the location of registration pins 520, upon the lower surface 530 of mask frame 150 are shown.

Figure 6A:
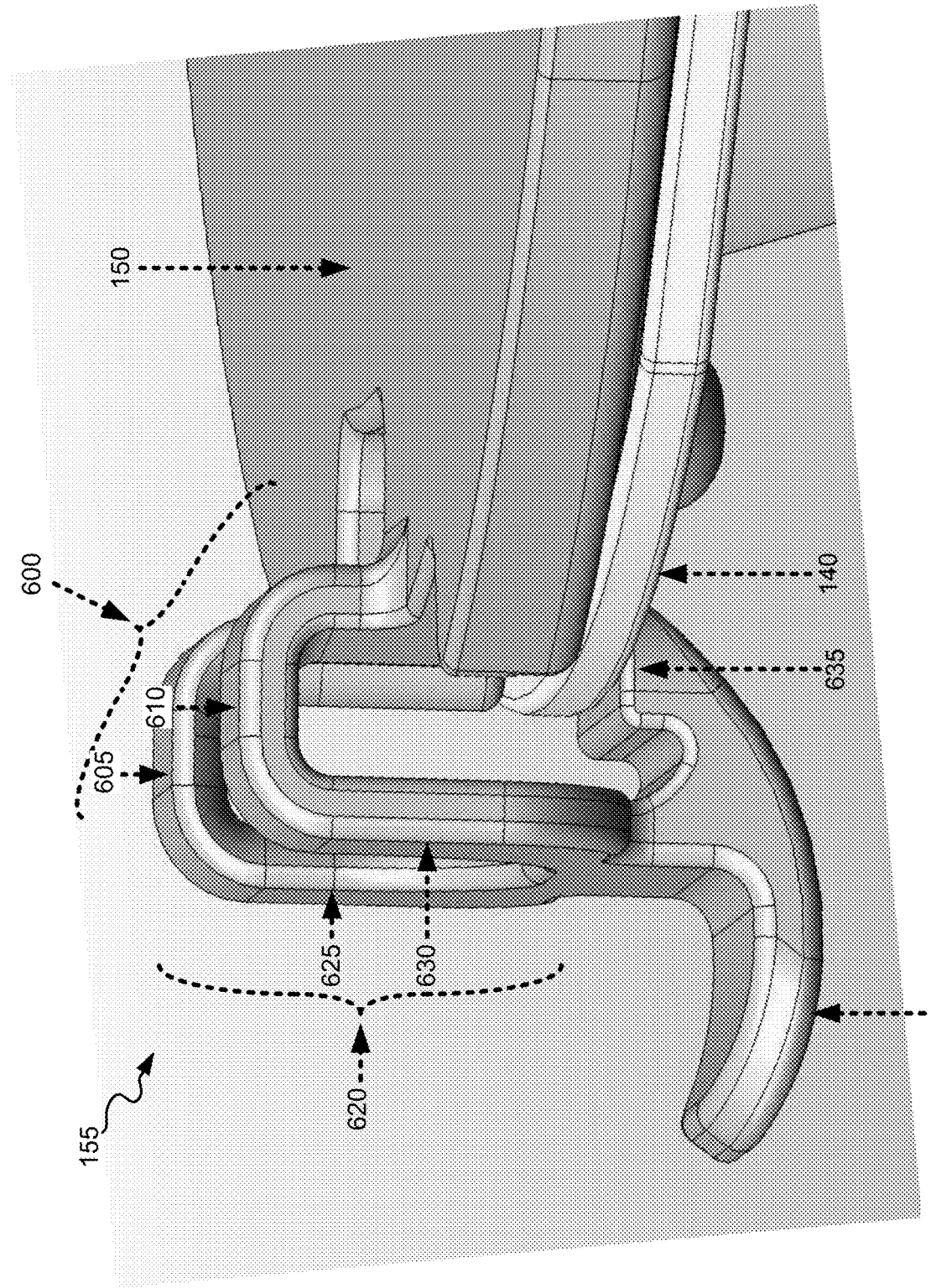
FIGS. 6A-6C depict details of the physical configuration of an exemplary embodiment of a spring clip, and a sequence of the process of unclipping the spring clip from the upper flange of the shell frame.
Figure 6B:
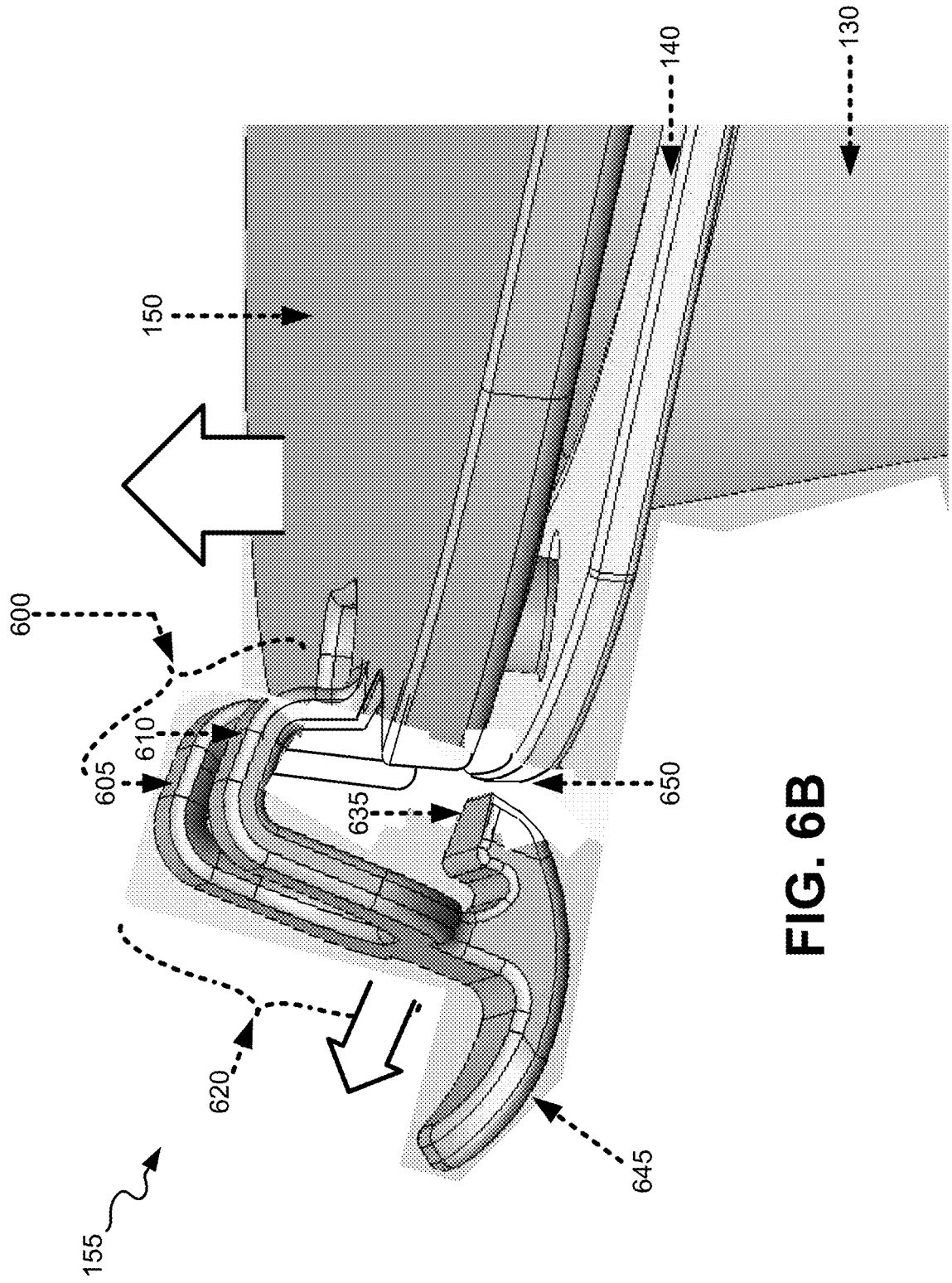
Figure 6C:
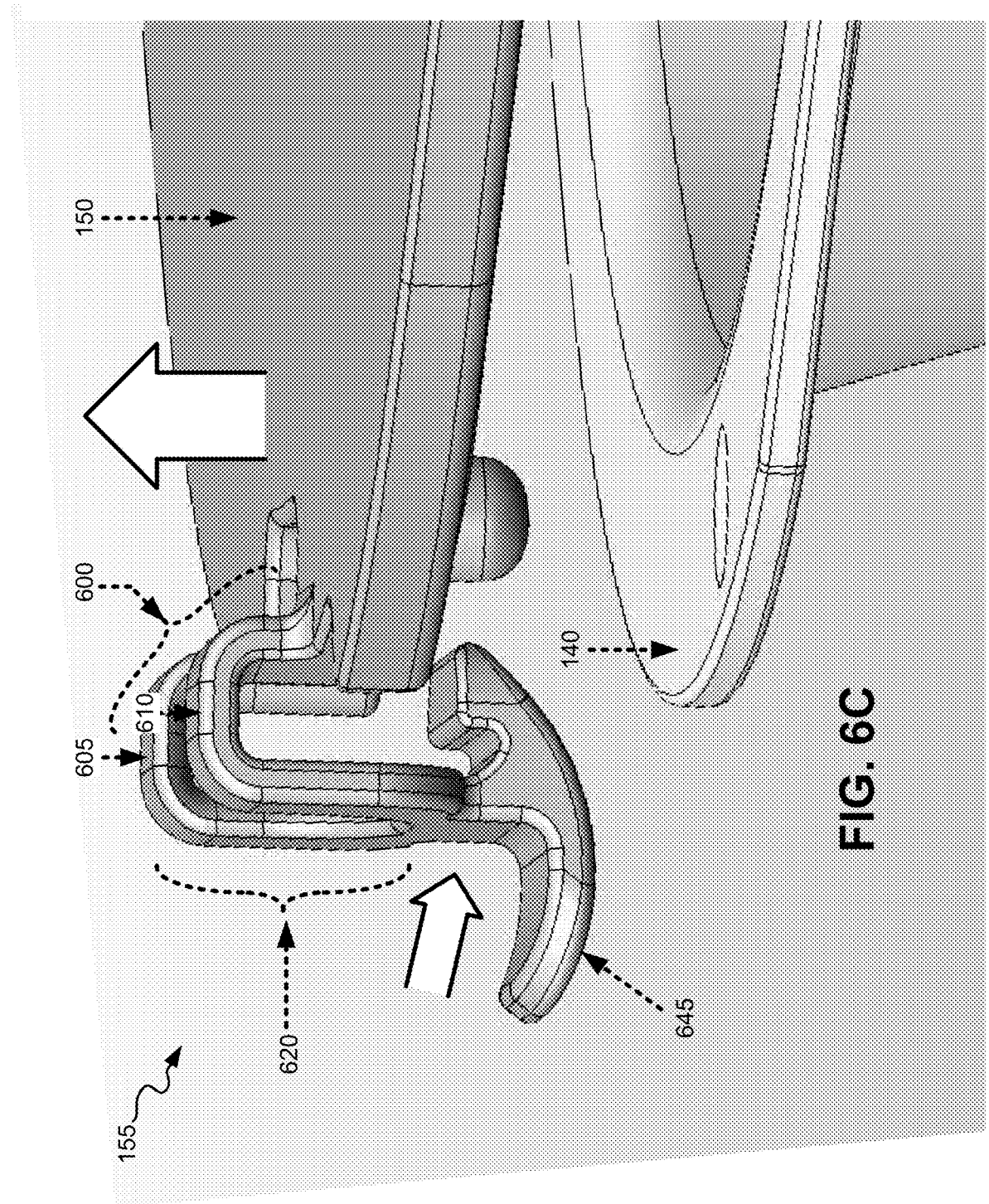

FIGS. 6A-6C depict details of a physical configuration of an exemplary embodiment of a spring clip 155, and a sequence of the process of unclipping a spring clip 155 from upper flange 140 of shell frame 130. FIG. 6A shows a close up view of spring clip 155 in which spring clip 155 has been clipped onto upper flange 140 to mount mask frame 150 onto shell frame 130. As shown in FIG. 6A, spring clip 155 includes two L-shaped spring arms 600 that attach to an outer edge of the upper surface of mask frame 150. Spring arms 600 include L-shaped spring arm 605 and L-shaped spring arm 610, which each connect to different, but adjacent, locations of the outer edge of the upper surface of mask frame 150. Spring arms 605 and 610 connect, at opposite ends from the ends connected to the upper surface of mask frame 150, to a U-shaped member 620 that further connects to spring clip knob 645 and to a mounting retention member 635. U-shaped member 620 includes two support members 625 and 630, where support member 625 connects to spring arm 605 and support member 630 connects to spring arm 610. Spring arms 605 and 610, as described further below with respect to FIGS. 6B and 6C, may flex in an outwards direction away from mask frame 150 to enable mounting retention member 635 to "clip" or "unclip" from a lower surface of upper flange 140 of shell frame 130.

FIG. 6B depicts an outward force being applied to spring clip knob 645 to cause spring arms 605 and 610 to flex outwards such that mounting retention member 635 is unclipped from flange 140 of shell frame 130. An individual using, for example, a thumb, may apply outward force on an upper or lower surface of spring clip knob 645. The outward force is transmitted up through support members 625 and 630 to spring arms 605 and 610 to cause spring arms 605 and 610 to flex in an outwards direction away from flange 140 of shell frame 130. As mounting retention member 635 moves outwards from shell frame 130, and out from under flange 140 of shell frame 130, spring clip 155 becomes "unclipped" from flange 140 of shell frame 130, and mask frame 150 may be lifted upwards to undock mask frame 150 from shell frame 130.

As further shown in FIG. 6C, once mask frame 150 has been lifted upwards such that mounting retention member 635 clears flange 140 of shell frame 130, the outward force applied to spring clip knob 645 may be discontinued and spring arms 605 and 610 may unflex and return to their normal, unflexed positions. To un-mount mask frame 150 from shell frame 130, one or more individuals can simultaneously apply an outward force to spring clip knobs 645 of each of the multiple spring clips 155 located on mask frame 150 (e.g., two spring clips 155 in the embodiment depicted in FIGS. 5A-5E), and then mask frame 150 can be lifted upwards away from shell frame 130 to undock mask frame 150 from shell frame 130. The sequence of the process of unclipping spring clip 155 from upper flange 140 of shell frame 130, as shown in FIGS. 6A-6C, may be reversed to clip the spring clip 155 to upper flange 140 of shell frame 130 when mask frame 150 is being docked with shell frame 130.

Figure 7:
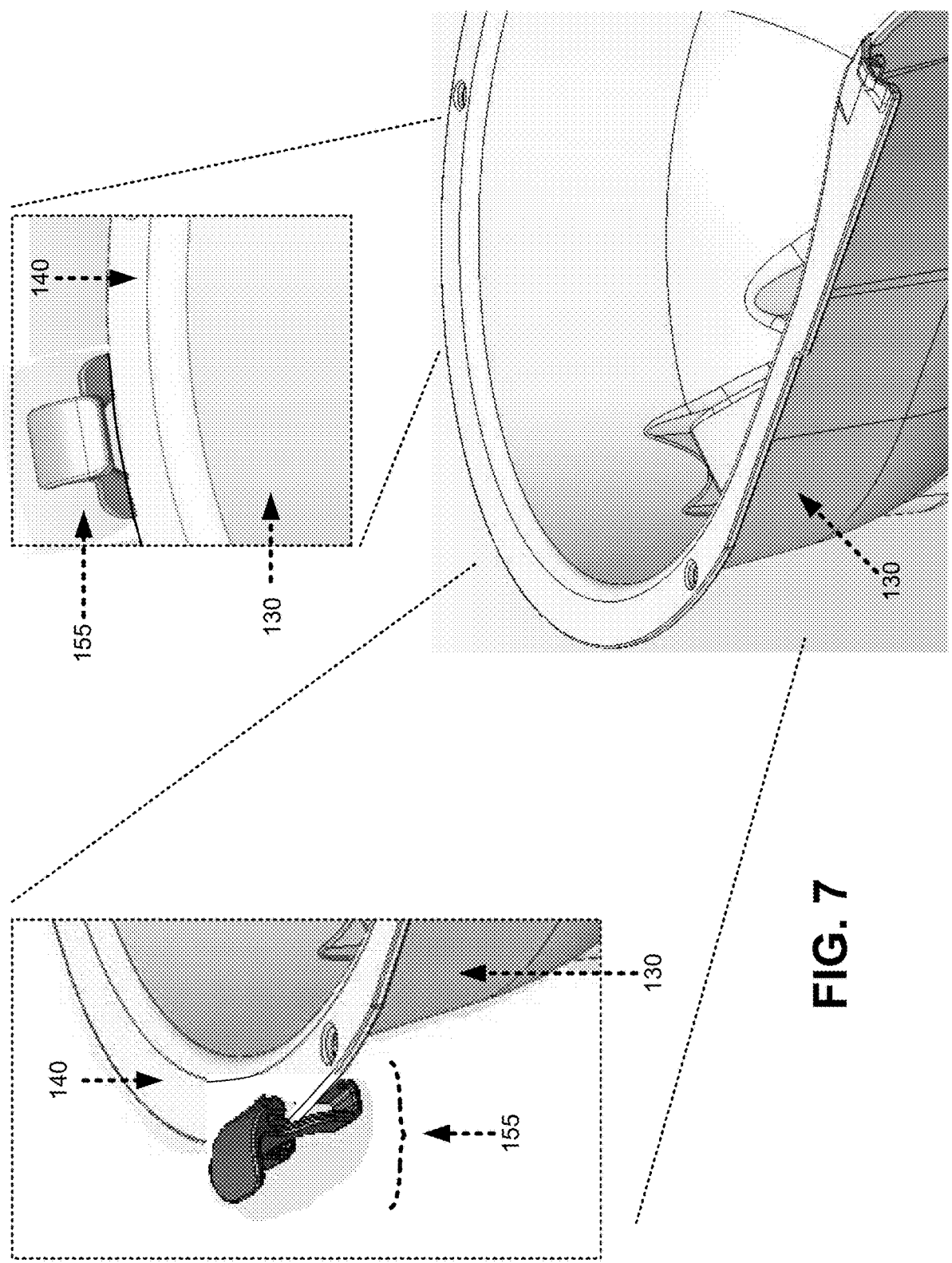
FIG. 7 illustrates an additional embodiment in which the spring clips reside on the shell frame, instead of the mask frame as described with respect to the embodiment of FIGS. 5A-5E.

FIG. 7 illustrates an additional embodiment in which the spring clips 155 reside on shell frame 130 instead of mask frame 150, as described with respect to the embodiment of FIGS. 5A-5E. In this embodiment, instead of clipping mask frame 150 to flange 140 of shell frame using spring clips 155 connected to an outer perimeter of mask frame 150, mask frame 150 is clipped to flange 140 of shell frame using spring clips 155 connected to an outer perimeter of upper flange 140 of shell frame 130. As seen in the two break-out views of FIG. 7, multiple spring clips 155 may be disposed at multiple locations around an outer perimeter of upper flange 140 of shell frame 130, and may each connect to a lower surface of upper flange 140 of shell frame 130. In one implementation, the multiple spring clips 155 may be integrally formed with shell frame 130 (i.e., formed from a single piece of material by injection molding, etc.). In another implementation, the multiple spring clips 155 may include separate clip units that may be fastened to the lower surface of the outer perimeter of flange 140 of shell frame 130 using various types of fastening mechanisms.

Figure 8:
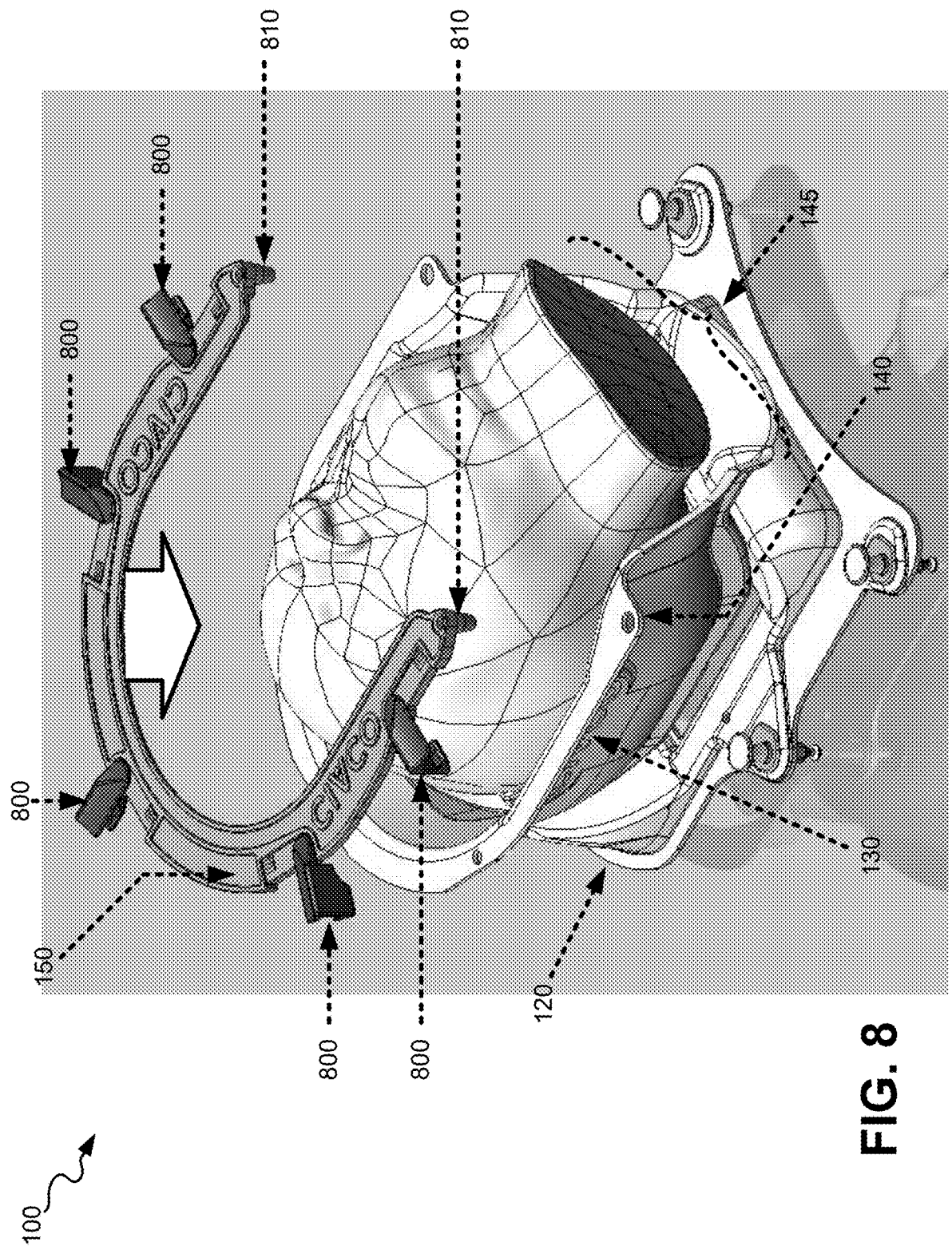
FIG. 8 depicts exemplary pivoting clamps mechanisms used to mount a mask frame to a shell frame according to another exemplary embodiment.

FIG. 8 depicts exemplary fastening mechanisms used to mount mask frame 150 to shell frame 130 according to another exemplary embodiment. While the structure of shell frame 130, and support base 120 of body part immobilization device 100 may be similar to previously described embodiments, the fastening mechanisms, in the exemplary embodiment shown in FIG. 8, include one or more pivoting clamps 800 and retention pins 810 instead of the spring clips previously described. As shown, mask frame 150 includes multiple pivoting clamps 800 which, in combination with retention pins 810, fasten mask frame 150 to shell frame 130, as described further below. Pivoting clamps 800, as depicted in FIG. 8, may be integral to mask frame 150. Each pivoting clamp 800 may include a pivot pin (not shown in FIG. 8), that inserts through a pivot hole (not shown) in mask frame 105. The pivot pin enables pivoting clamp 800 to pivot about an axis, that corresponds to the pivot hole, to enable a clamping arm of the pivoting clamp 800 to clamp onto the upper flange 140 of shell frame 130, thereby fastening mask frame 150 to shell frame 130. FIG. 8 depicts mask frame 150 in an initial elevated position, above the upper flange 140 of shell frame 130, prior to lowering of mask frame 150 to contact the upper flange 140 of shell frame 130 to dock mask frame 150 with shell frame 130. FIG. 8 depicts one implementation in which mask frame 150 includes five different pivoting clamps 800 spaced around the perimeter of mask frame 150. However, in other implementations, fewer, or more, pivoting clamps 800 may be used for fastening mask frame 150 to shell frame 130 when mask frame 150 is docked with shell frame 130.

FIGS. 9A and 9B depict further details of the configuration of, and operation of, a pivoting clamp 800 of the exemplary embodiment of FIG. 8. As shown in FIGS. 9A and 9B, the pivoting clamp 800 pivots about an axis formed by a pivot pin 910 of pivoting clamp 800 that is inserted through a pivot hole 920 within mask frame 150. In a fully "open" pivot position, as shown in FIG. 9A, pivoting clamp 800 may form an approximate acute angle (e.g., 90 degrees or less) with mask frame 150. From the "open" pivot position, pivoting clamp 800 rotates to "close" within a pivot slot 900 formed within mask frame 150. As depicted in FIG. 9B, pivoting clamp 800 may include an upper clamping arm 930 and a lower clamping arm 940. As described in further detail below, upper clamping arm 930 and lower clamping arm 940 operate together, when pivoting claim 800 is in a closed position within pivot slot 900, to clamp mask frame 150 to upper flange 140 of shell frame 130 (not shown in FIGS. 9A and 9B).

FIGS. 9C and 9D depict additional details of the mounting of pivoting clamp 800 to mask frame 150. As shown in FIG. 9C, pivot pin 910 of pivoting clamp 800 inserts, via an upper surface of mask frame 150, into pivot hole 920 that may be formed within pivot slot 900. Pivot hole 920 may extend through mask frame 150 between the upper surface of mask frame 150 and a lower surface of mask frame 150. In one implementation, pivot pin 910 may be configured in approximately a cylindrical shape having dimensions that fit relatively tightly within a circular shape of pivot hole 920, but such that pivot pin 910 may pivot about an axis within the center of pivot pin 910 within pivot hole 920.

FIGS. 10A-10C depict a physical configuration of an exemplary implementation of pivoting clamp 800. Pivoting clamp 800 may include a pivot arm 1000 upon which upper clamping arm 930, pivot pin 910, and lower clamping arm 940 are formed or mounted. In the implementation depicted in FIGS. 10A-10C, pivoting clamp 800 is formed from a single piece of material. In other implementations, pivoting clamp 800 may be formed from separate components that are attached, affixed, or mounted to pivot arm 1000. As can be seen in FIGS. 10A and 10C, a clamping space 1010 may reside between upper clamping arm 930 and lower clamping arm 940, where a width of clamping space 1010 approximately equals a combined thickness of mask frame 150 and upper flange 140 of shell frame 130 (not shown in FIGS. 10A-10C). The width of clamping space 1010, therefore, permits mask frame 150 and upper flange 140 of shell frame 130 to fit within clamping space 1010, between upper clamping arm 930 and lower clamping arm 940, to tightly clamp and fasten mask frame 150 in place against the upper surface of upper flange 140 of shell frame 130.

In some implementations, as shown in FIGS. 10A and 10C, upper clamping arm 930, clamping space 1010, and lower clamping arm 940 may form, when viewed from one side, roughly a bracket-like structure that enables pivot slot 900 of mask frame 150 and upper flange 140 of shell frame 130 to fit within the bracket-like structure as pivoting clamp 800 is rotated to close with pivot slot 900 of mask frame 150. On an underside of pivot arm 1000, within clamping space 1010, a clamping detent 1020 may be disposed that acts to hold pivoting clamp 800 in position against an upper surface of mask frame 150 within pivot slot 900 when pivoting clamp 800 is rotated to "close" pivoting clamp 800 in a clamping position within pivot slot 900.

As further depicted in FIGS. 10A, 10B, and 10C, pivot pin 910 may include a bifurcated cylindrical shape that permits the bifurcated halves of the cylinder of pivot pin 910 to flex inwards and outwards when pivot pin 910 is inserted into pivot hole 920, or when pivot pin 910 is pulled out of pivot hole 920. In some implementations, pivot pin 910 may include retention "nubs," that mate with corresponding nub slots within pivot hole 920, so as to retain pivot pin 910 within pivot hole 920 as pivoting clamp 800 is rotated through a certain range of rotated positions within pivot hole 920.

Figure 11:
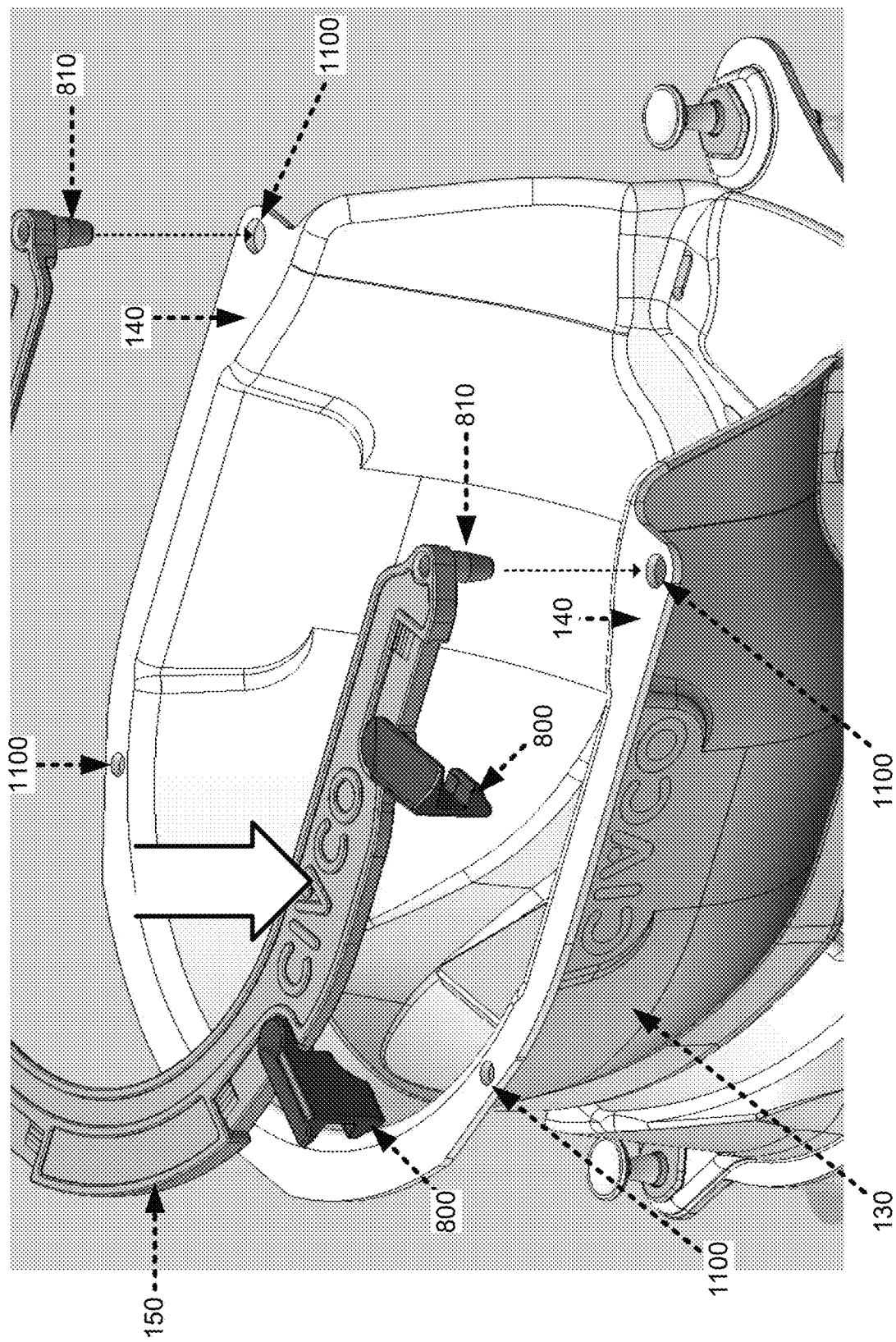
FIGS. 11, 12A, 12B, 13, and 14A-14D depict a sequence associated with mounting the mask frame to the shell frame, of the exemplary embodiment shown in FIG. 8, when the mask frame is docked with the shell frame.
Figure 12:
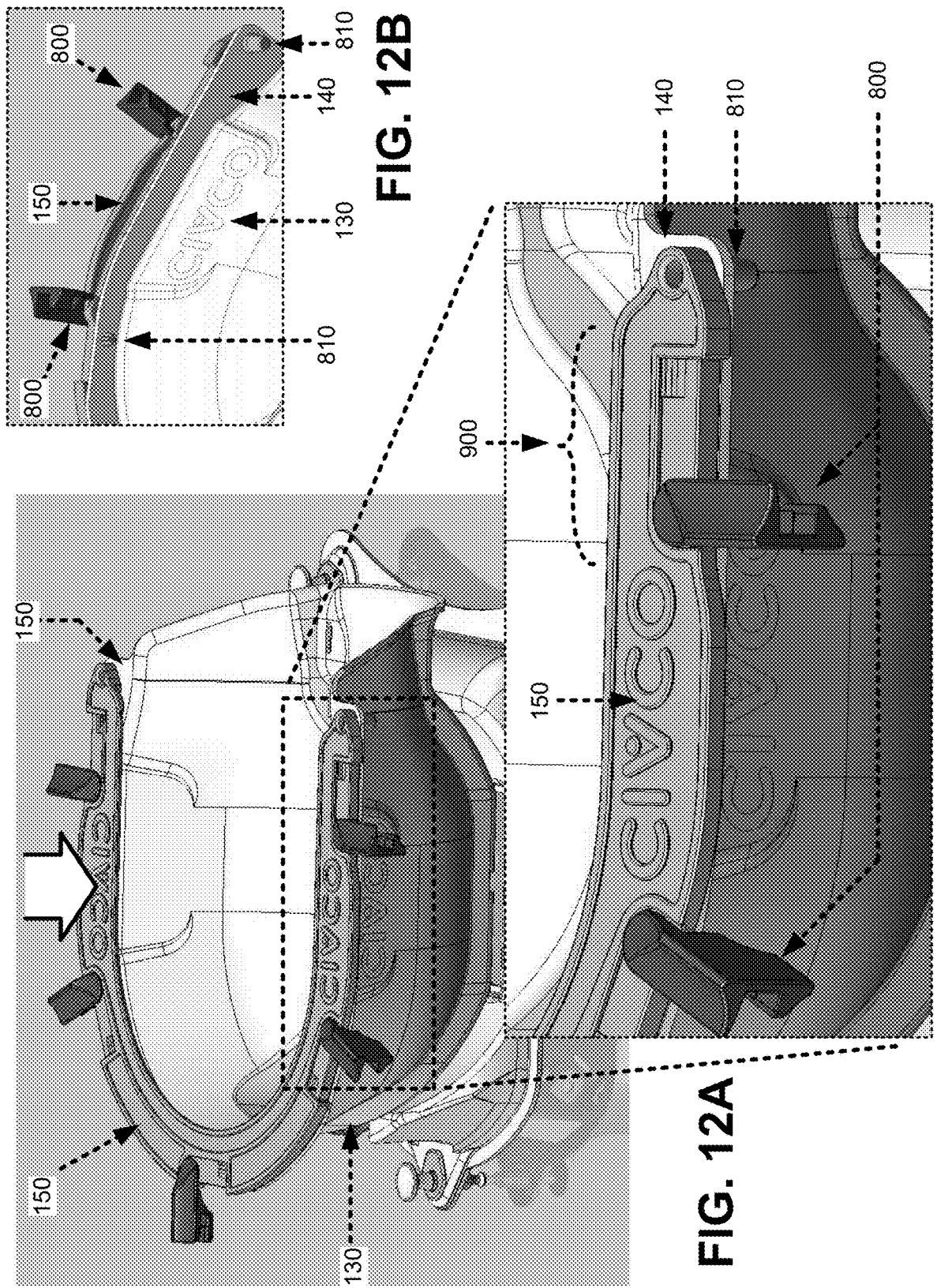

FIGS. 11, 12A, 12B, 13, and 14A-14D depict a sequence associated with mounting mask frame 150 to shell frame 130, of the exemplary embodiment shown in FIG. 8, when mask frame 150 is docked with shell frame 130. As depicted in FIG. 11, mask frame 150 is initially positioned over upper flange 140 of shell frame 130 such that multiple retention pins 810 on the underside of mask frame 150 are aligned directly over corresponding retention holes 1100 that extend through upper flange 140 of shell frame 130. As further shown in FIGS. 12A and 12B, mask frame 150 is lowered upon shell frame 130 such that the underside of mask frame 150 contacts the upper surface of upper flange 140 of shell frame 130, and retention pins 810 are inserted through the retention holes 1100 in the upper flange 140 of shell frame 130. Upon the lowering of mask frame 150 upon shell frame 130, pivoting clamps 800, as shown in FIGS. 12A and 12B, are still in the open position.

Figure 13:
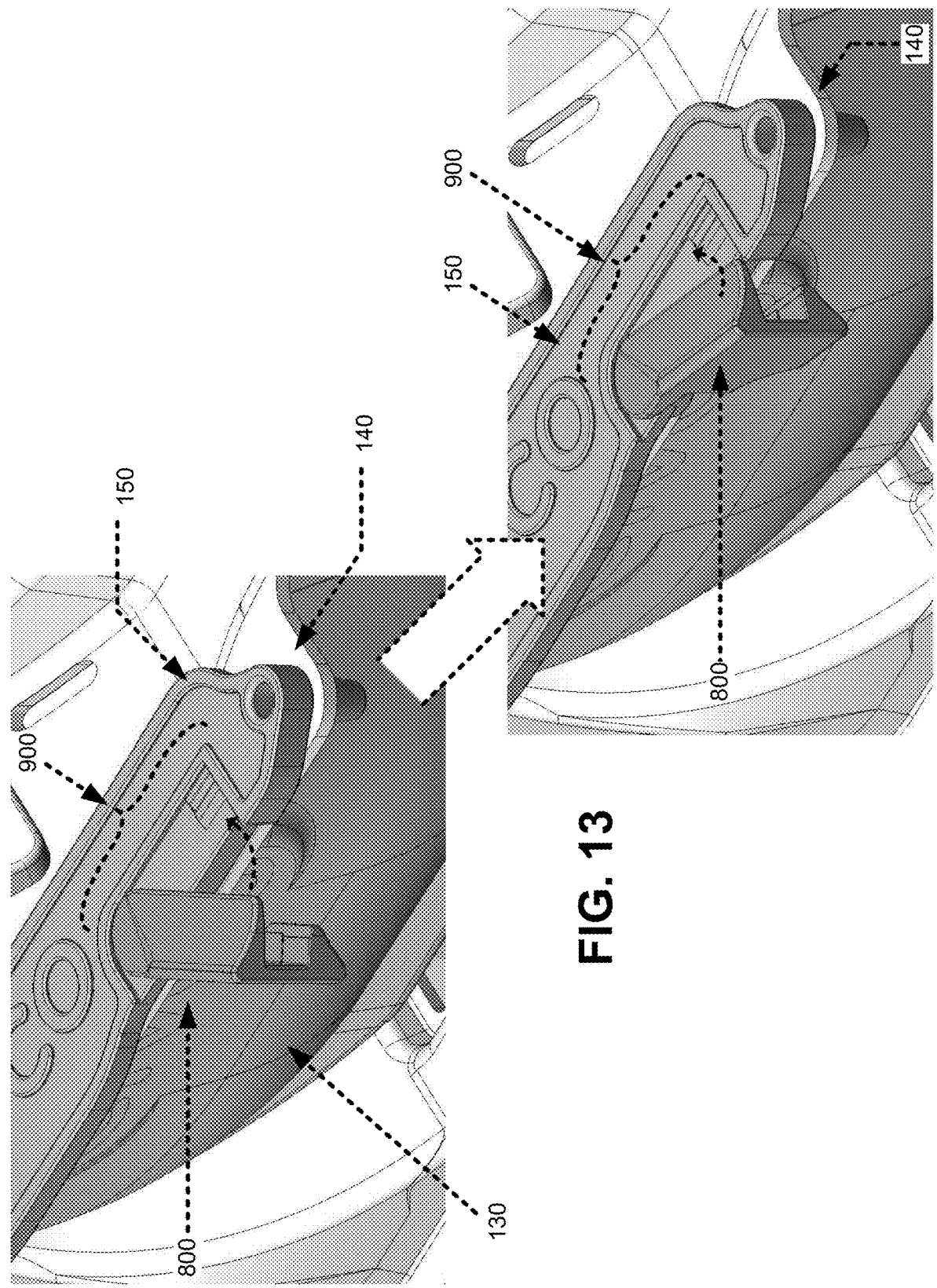

As further depicted in FIG. 13, subsequent to lowering mask frame 150 upon the upper flange 140 of shell frame 130 to dock mask frame 150 with shell frame 130, the pivoting clamps 800 may be rotated about axes formed within respective pivot pins 910 and pivot holes 920. As pivoting clamps 800 are rotated inwards towards mask frame 150, the bracket-like structure of pivot arm 1000 of pivoting clamp 800 clamps, as pivoting clamp 800 enters pivot slot 900, around the thickness of mask frame 150 and the thickness of upper flange 140 of shell frame 130.

Figure 14C:
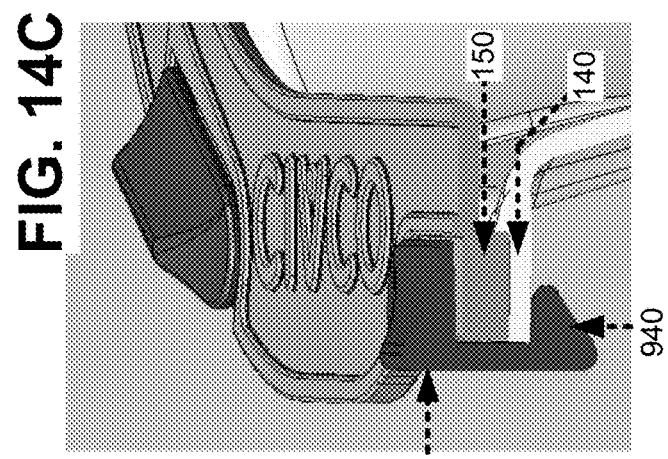
Figure 14A:
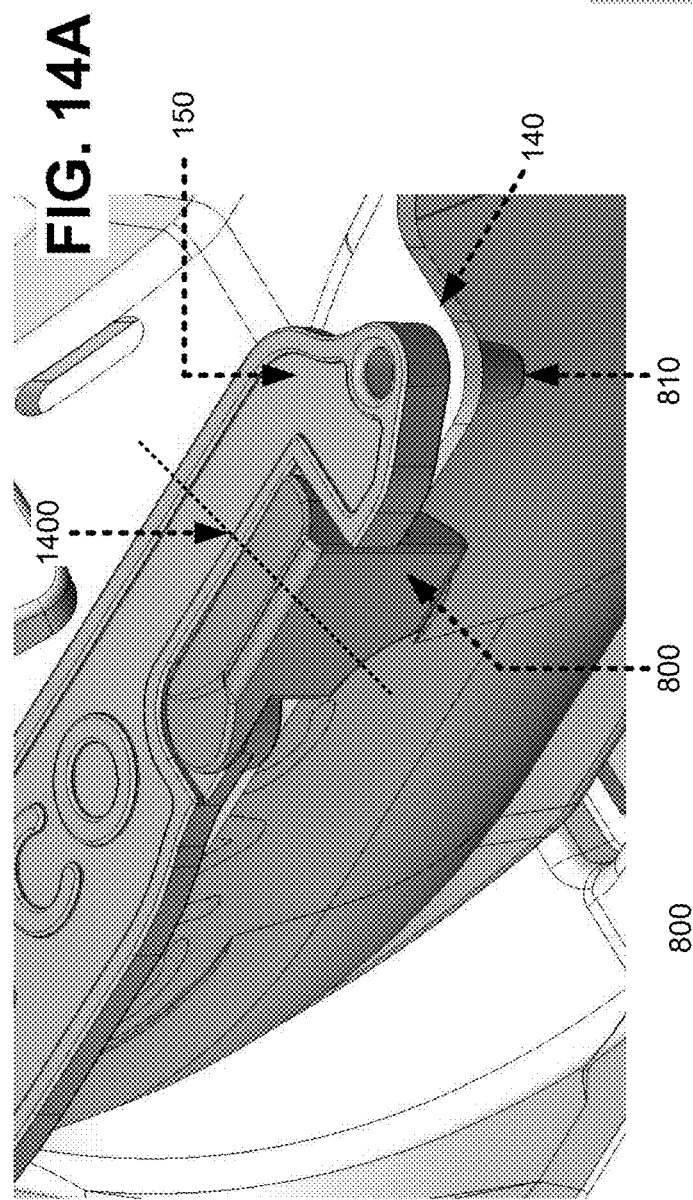
Figure 14B:
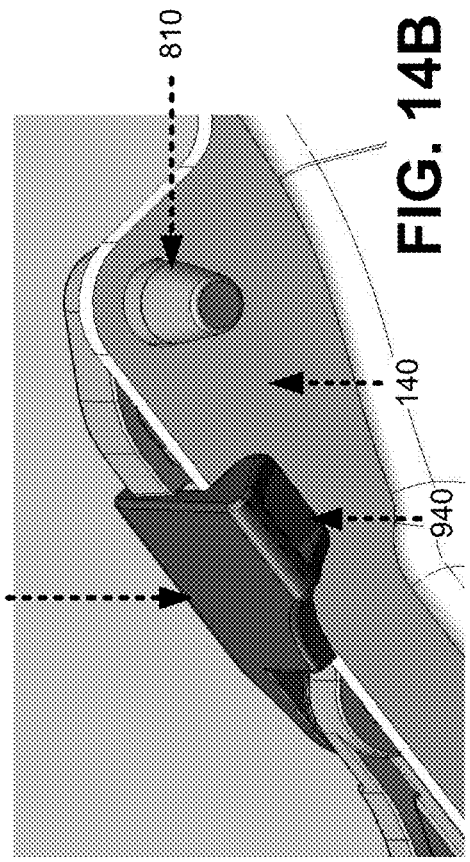
Figure 14D:
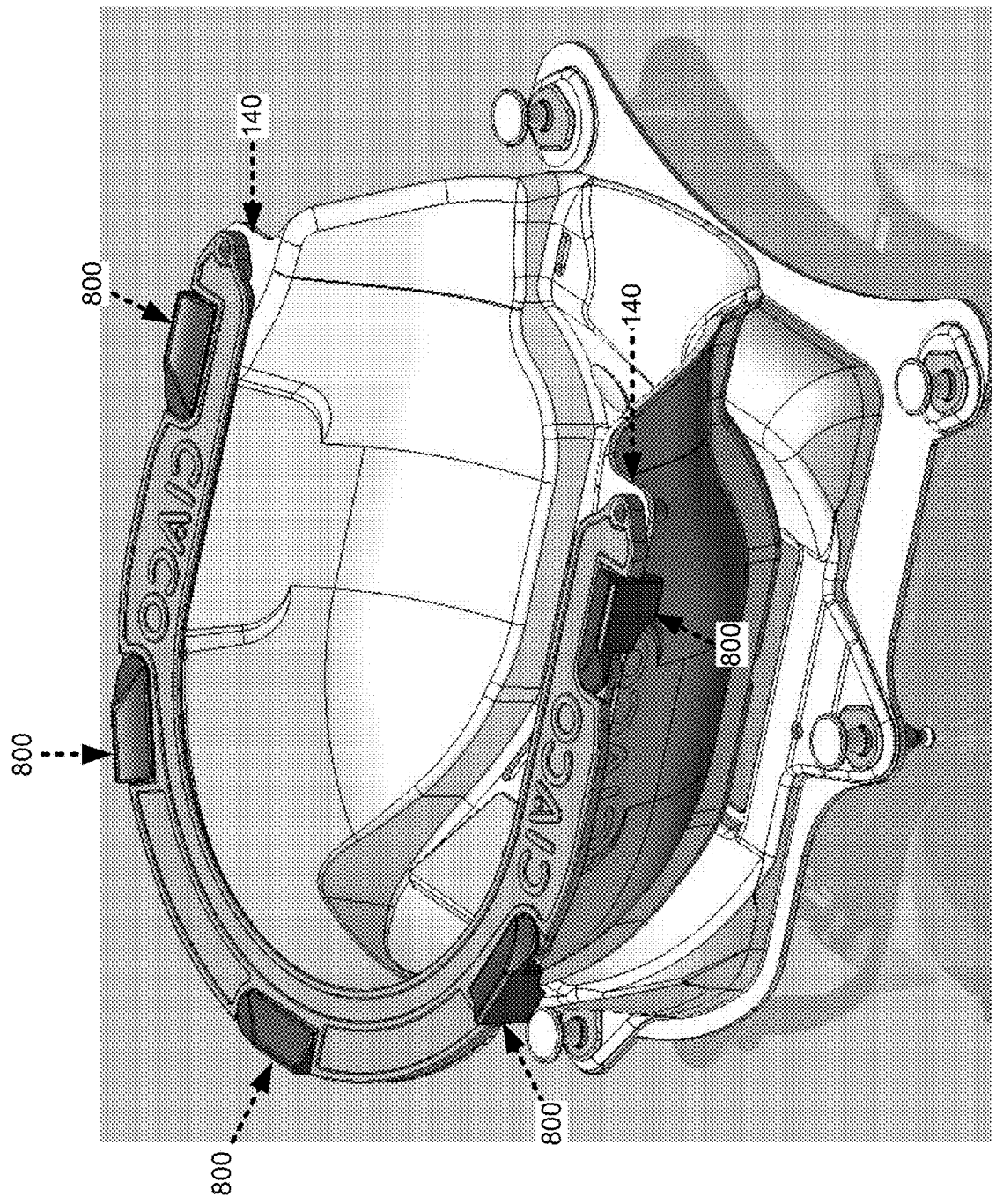

FIGS. 14A-14D depict different views of mask frame 150 and shell frame 130 when pivoting clamps 800 have been closed to a clamped position, clamping the lower surface of mask frame 150 against the upper surface of upper flange 140 of shell frame 130. FIG. 14C shows a cross-sectional view that corresponds to the cross-section line 1400 through pivoting clamp 800 shown in FIG. 14A. As can be seen in the cross-sectional view of FIG. 14C, the thickness of mask frame 150 and the thickness of flange 140 of shell frame 130 tightly fit within the clamping space 1010 between upper clamping arm 930 and lower clamping arm 940 of pivot arm 1000, where the fit enables clamping detent 1020 (shown in FIG. 10C) to hold pivoting clamp 800 in position against an upper surface of mask frame 150 within pivot slot 900.

The sequence of FIGS. 11, 12A, 12B, 13, and 14A-14D, associated with mounting mask frame 150 to shell frame 130, may be reversed (i.e., performed in reverse order) to un-mount mask frame 150 from shell frame 130 after opening the pivoting clamps 800 of the exemplary embodiment of FIG. 8.

FIG. 15 depicts a further exemplary embodiment in which the body part immobilization device includes a body part immobilization table 1505, and in which a multi-piece mask frame 1500, having clips or clamps, may be used to attach to the body part immobilization table 1505 such that the mask material of the multi-piece mask frame 1500 form fits to the body part and immobilizes the body part upon the body part immobilization table 1505. As shown, a multi-piece mask frame 1500 may be positioned over body part immobilization table 1505, and lowered into position upon the table 1505 to form fit the material of the mask (not shown) over the body part (not shown) being immobilized.

In the embodiment shown in FIG. 15, multi-piece mask frame 1500 includes separate frame pieces 1510-1, 1510-2 and 1510-3 (referred to collectively as "frame pieces 1510" or individually as "frame piece 1510" or "frame piece 1510-x"), with each frame piece 1510 including at least one clip or clamp (a clamp is shown by way of example) for attaching the frame piece 1510 to the body part immobilization table 1505. In other embodiments, the mask frame 1500 may include a single, continuous frame with multiple clips or clamps disposed at different locations upon the continuous frame. Each frame piece 1510 of multi-piece mask frame 1500 may include retention pins (not shown in FIG. 15) that extend from a surface of frame piece 1510 to dock with an upper surface of body part immobilization table 1505. The retention pins, when the frame piece 1510 is docked with body part immobilization table 1505, extend into corresponding pin retention holes 1520 to hold the frame piece 1510 in position upon the upper surface of the table 1505. Subsequent to docking of the frame pieces 1510 of mask frame 1500 with body part immobilization table 1505, the clips or clamps (clamps shown in FIG. 15) may be engaged with a corresponding engagement flange 1530 of table 1505. FIG. 15 depicts a single engagement flange 1530, on the underside of table 1505, for engaging a clamp of a single mask piece 1510 of mask frame 1500. Each clamp of mask frame 1500, however, has a corresponding engagement flange 1530 at an appropriate location on the underside of table 1505. Body part immobilization table 1505 is depicted in FIG. 15 as including a shape for receiving a head of a patient for immobilization and testing. Table 1505 may, however, include other shapes for receiving other, different body parts (e.g., arms, hands, feet, chest area, etc.).

FIGS. 16A and 16B depict different views of a single frame piece 1510 of the multi-piece mask frame 1500 of FIG. 15. As shown, frame piece 1510 includes a pivoting clamp 1600 that attaches to an L-shaped body 1605 of frame piece 1510. L-shaped body 1605 of frame piece 1510 may include a base 1610, a mask attachment bracket 1615, and a pivoting clamp 1600. Base 1610 may include multiple retention pins 1650 disposed on an underside of base 1610. Retention pins 1650 insert within retention holes 1520 of body part immobilization table 1505 (shown in FIG. 15) to maintain the frame piece 1510 in a position upon table 1505. Mask attachment bracket 1615 includes a mask attachment mechanism, such as a bracket structure shown in FIGS. 16A and 16B, that attaches the sheet of mask material (e.g., a thermoplastic sheet) to frame piece 1510. One end of the sheet of mask material (not shown) may fit, and be fastened, within the slot of the bracket of the mask attachment mechanism. Various different fastening mechanisms may be used to fastening the sheet of mask material within the slot of the bracket attachment mechanism, such as glue, fastening pins or screws, etc.

Pivoting clamp 1600 may include a pivot pin 1620 (shown in FIG. 16B), that inserts through a pivot hole in the base 1610 of L-shaped body 1605 of frame piece 1510. The pivot pin 1620 enables pivoting clamp 1600 to pivot about an axis, that corresponds to the pivot hole, to enable a clamping arm of the pivoting clamp 1600 to clamp onto the flange 1530 of table 1505, thereby attaching frame piece 1510 to table 1505.

As depicted in FIG. 16A, pivoting clamp 1600 may include an upper clamping arm 1625 and a lower clamping arm 1630, which define a clamping space 1635. As described in further detail below, upper clamping arm 1625 and lower clamping arm 1630 operate together, when pivoting clamp 1600 is in a closed position, to clamp frame piece 1510 to flange 1530 of body part immobilization table 1505 (not shown in FIGS. 16A and 16B). Clamping space 1635, which resides between upper clamping arm 1625 and lower clamping arm 1630, and a width of clamping space 1635 may be approximately equal to a combined thickness of base 1610 of L-shaped body 1605 and flange 1530 of table 1505 (not shown in FIGS. 16A and 16B). Upper clamping arm 1625, clamping space 1635, and lower clamping arm 1630 may form, when viewed from one side, roughly a bracket-like structure that enables a thickness of base 1610 of frame piece 1510 and flange 1530 of table 1500 to fit within the bracket-like structure as pivoting clamp 1600 is rotated to a closed position.

On an underside of the pivot arm of clamp 1600 within clamping space 1635 a clamping detent 1640, shown in FIG. 16B, may be disposed that acts to hold pivoting clamp 1600 in position against an upper surface of base 1610 of frame piece 1510 when pivoting clamp 1600 is rotated to "close" pivoting clamp 1600 in a clamped position. The width of clamping space 1635, therefore, permits frame piece 1510 and flange 1530 of body part immobilization table 1505 to fit within clamping space 1635, between upper clamping arm 1625 and lower clamping arm 1630, to tightly clamp, in conjunction with the operation of clamping detent 1640, frame piece 1510 in place against the upper surface of table 1505.

FIGS. 17A, 17B, and 17C depict an exemplary sequence associated with using a pivoting clamp 1600 to fasten a single frame piece 1510 of multi-piece mask frame 1500 to body part immobilization table 1505. After docking frame piece 1510 with body part immobilization table 1505, pivoting clamp 1600, as shown in FIGS. 17A and 17B, may be pivoted towards (shown with an arrow in FIGS. 17A and 17B) a lateral edge of base 1610 of mask piece 1510 and flange 1530 of table 1505. As pivoting clamp 1600 closes, clamping space 1635 encloses the lateral edge of base 1610 of frame piece 150 and engagement flange 1530 of table 1500 such that clamping detent 1640 (not shown), on the underside of upper clamping arm 1625 of pivoting clamp 1600 acts to hold pivoting clamp 1600 in a clamped or closed position against the upper surface of base 1610, thereby securing base 1610 in a docked and attached position against the upper surface of body part immobilization table 1505. In other implementations (not shown), tightening mechanisms, in addition to, or as an alternative to, clamping detent 1640 may be used with pivoting clamps 1600 to tighten the clamp in the clamped or closed position. Such tightening mechanisms may include, for example, tightening screws.

Figure 18:
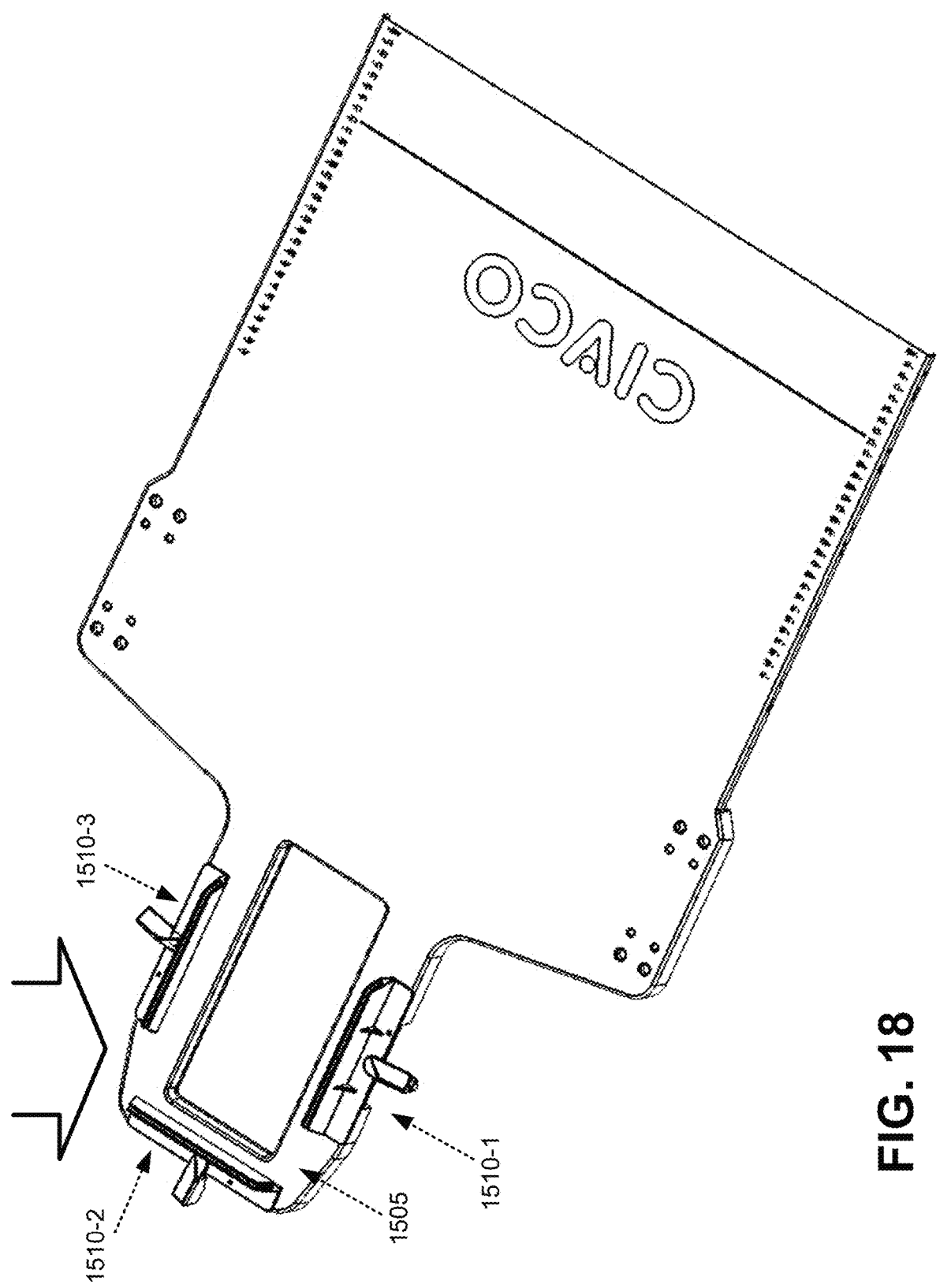
FIGS. 18-21 illustrate an exemplary sequence associated with docking the multi-piece mask frame of FIG. 15 to the body part immobilization table.

FIGS. 18-21 illustrate an exemplary sequence associated with docking the multi-piece mask frame 1500 to body part immobilization table 1505. As shown in FIG. 18, each of the multiple separate pieces 1510 of the multi-piece mask frame 1500 may be lowered on each side of the body part (not shown) and placed upon table 1505, to dock with the table 1505, causing the mask material (not shown) to form fit to the body part. In the exemplary embodiment shown in FIG. 18, the multi-piece mask frame 1500 includes three frame pieces 1510-1, 1510-2, and 1510-3, with each frame piece 1510 including its own pivoting clamp 1600 for attaching to table 1505. As further shown in FIGS. 19-21, pivoting clamp 1600-1 of frame piece 1510-1, pivoting clamp 1600-2 of frame piece 1510-2, and pivoting clamp 1600-3 of frame piece 1510-3 may each be pivoted inwards towards a respective engagement flange 1530 of table 1505 (only flange 1530, adjacent to pivoting clamp 1600-1, can be seen in FIGS. 19-21).

Figure 21:
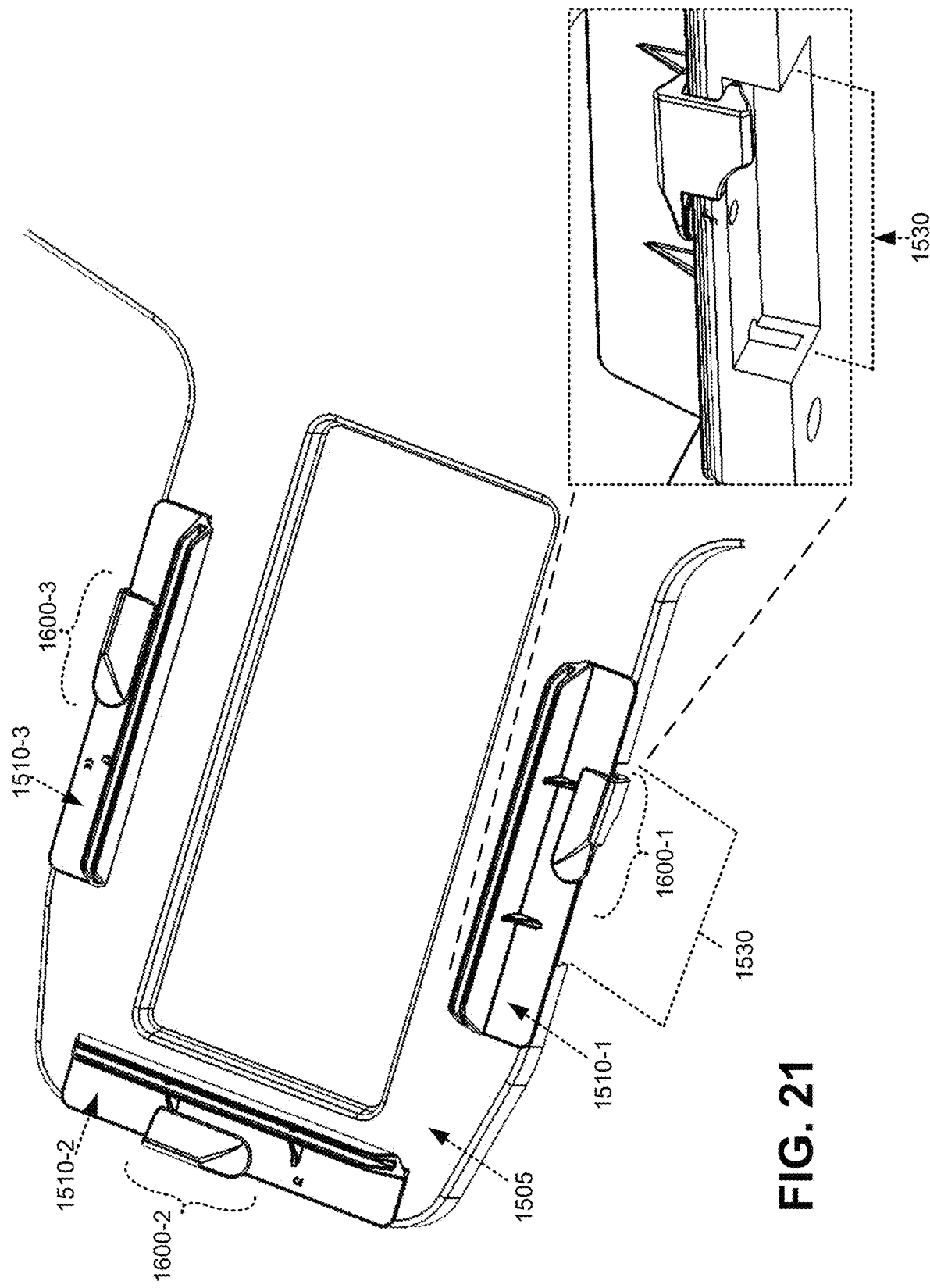
Figure 22:
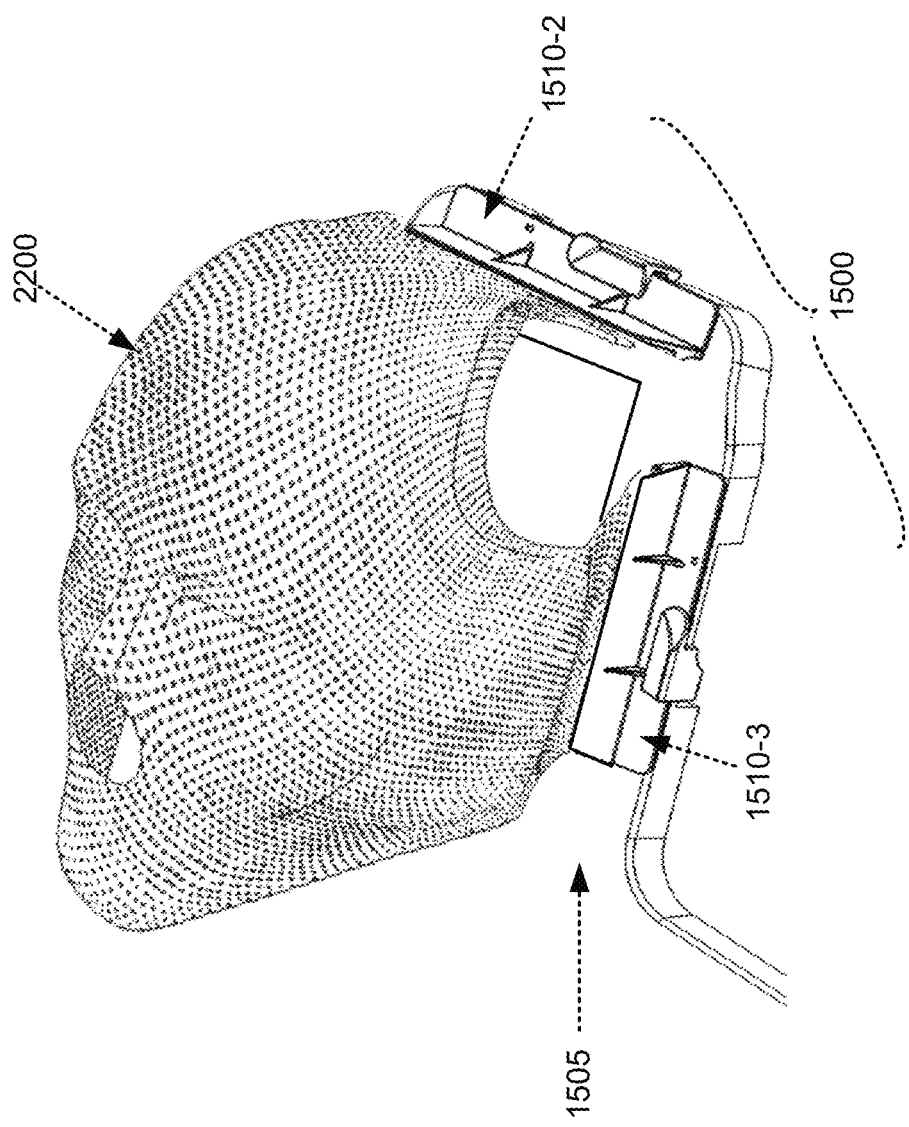
FIG. 22 illustrates the multi-piece mask frame of FIG. 15 in a docked and attached position upon the body part immobilization table with the mask material form fitted to the body part of the patient upon the table.

Docking and attachment of multi-piece mask frame 1500 concludes, as shown in FIG. 21, with pivoting clamps 1600-1, 1600-2, and 1600-2 closing to a clamped position to attach a respective frame piece 1510 to body part immobilization table 1505. As illustrated, the outside of clamp 1600 is parallel and essentially flush with base 1610 of frame piece 1610. FIG. 22 illustrates multi-piece mask frame 1500 in a docked and attached position upon table 1505, with the mask material 2200, connected to frame pieces 1510-1 (not shown), 1510-2 and 1510-3, and form fitted to the body part (e.g., a human head) of the patient upon table 1505. In embodiments in which the mask material 2200 includes a thermoplastic material, form fitting the mask material to the body part to immobilize the body part upon table 1505 includes stretching the thermoplastic material over the body part and then docking and attaching the separate frame pieces 1510 to body part immobilization table 1505 using the pivoting clamps 1600.

Figure 19:
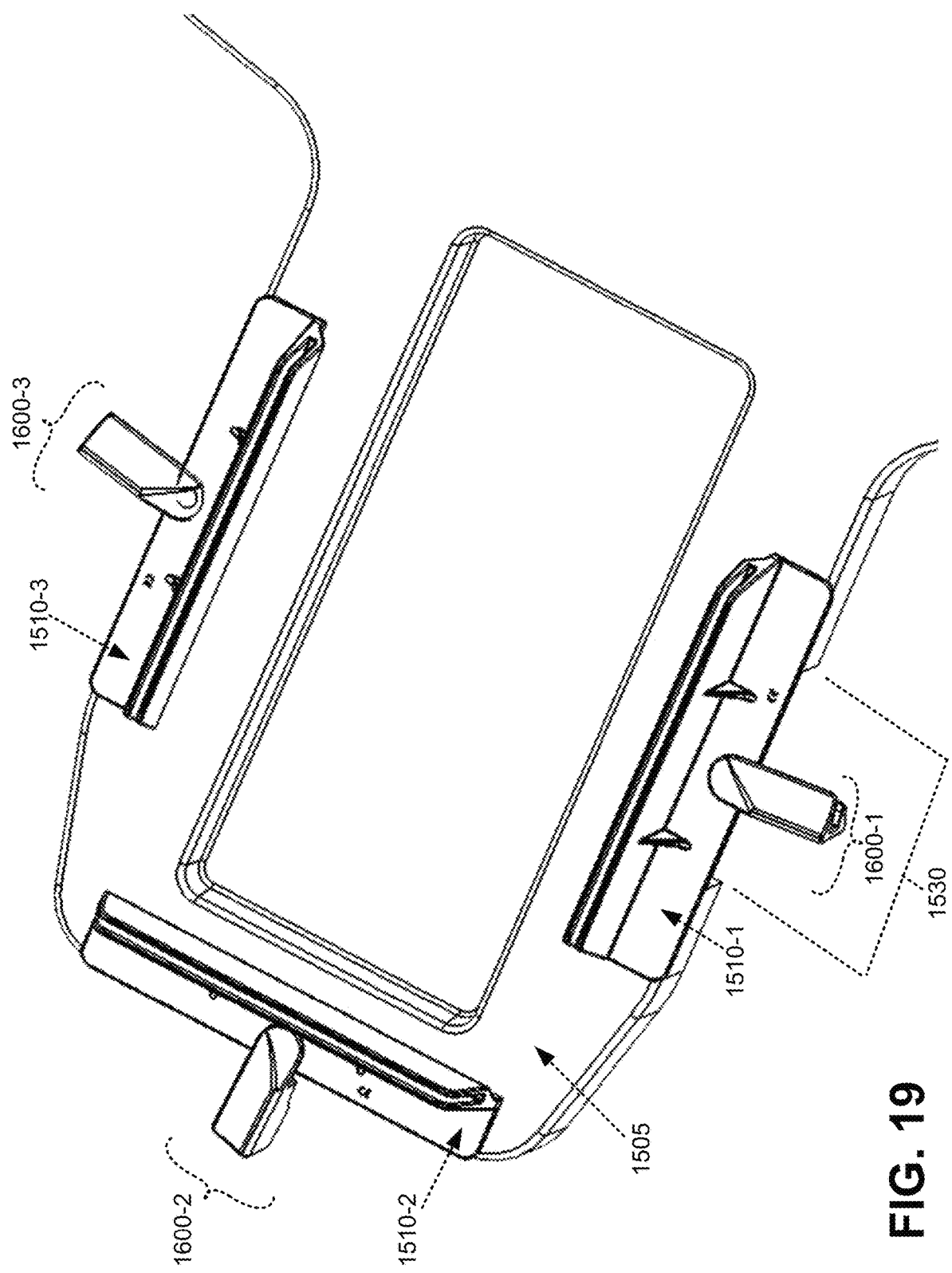
Figure 20:
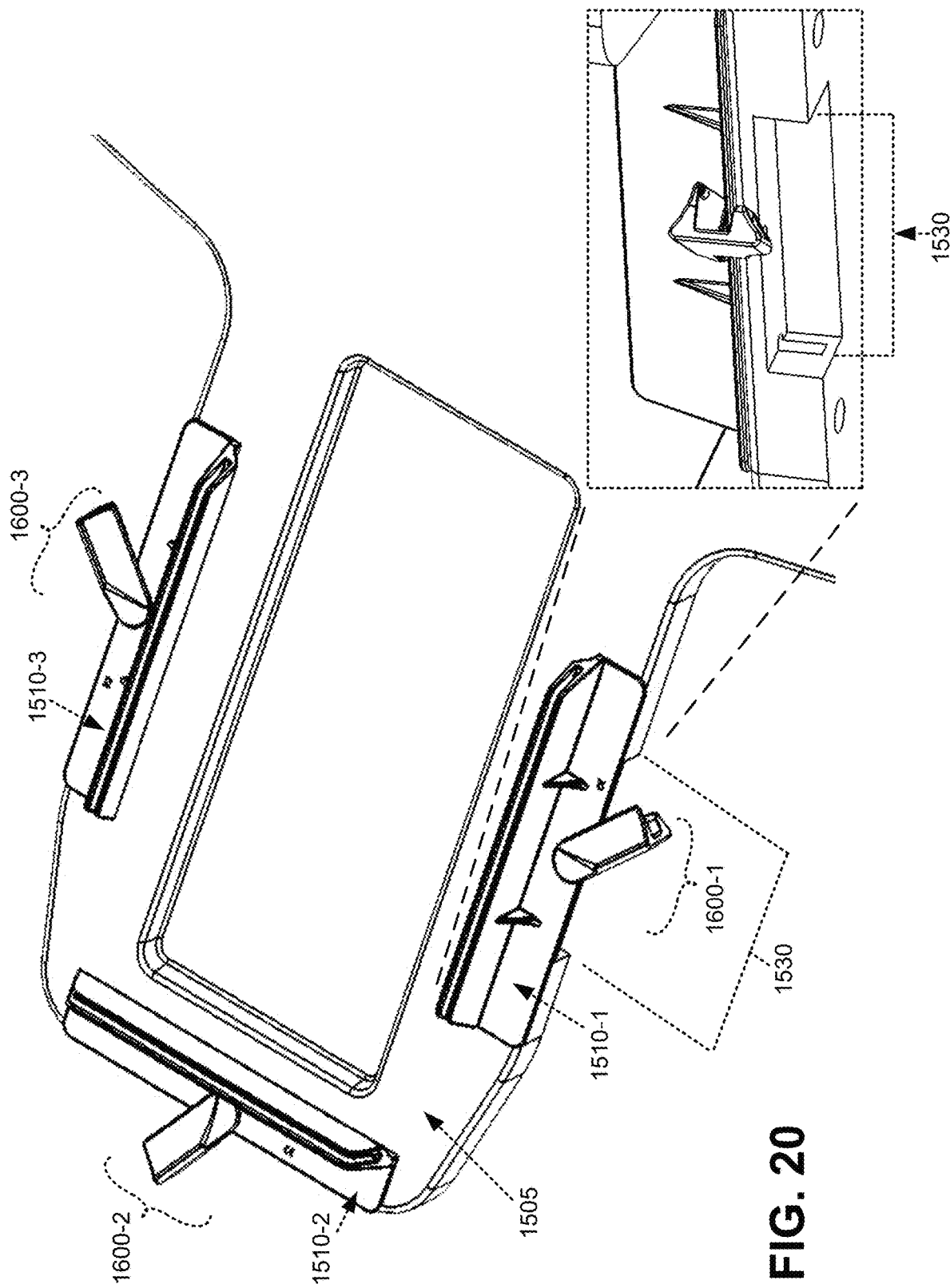

The sequence of FIGS. 19, 20, and 21, associated with docking multi-piece mask frame 1500 to body part immobilization table 1505, may be reversed (i.e., performed in reverse order) to un-dock mask frame 1500 from table 1505 after opening the pivoting clamps 1600 and detaching the frame pieces 1510 from engagement flanges 1530 of table 1505.

The foregoing description of implementations provides illustration and description, but is not intended to be exhaustive or to limit the invention to the precise form disclosed. Modifications and variations are possible in light of the above teachings or may be acquired from practice of the invention. For example, though some of the embodiments have been depicted and described herein with two clips 155, in alternative embodiments more than two clips (e.g., 3 or 4), or only a single clip may be used for attaching mask frame 150 to shell frame 130, or to a different structure. Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention. Therefore, the above-mentioned description is to be considered exemplary, rather than limiting, and the true scope of the invention is that defined in the following claims.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise. As used herein, "exemplary" means "serving as an example, instance or illustration."

What is claimed is:

1. A mask structure, comprising:
   a first frame having a shape to fit around, or over, a body part, the first frame further comprising a first surface configured to dock with a docking surface of a second frame that receives and supports the body part, wherein the docking surface comprises an upper flange of the second frame, and wherein the first frame comprises an outer, lateral edge and an inner, lateral edge;
   a material attached to the first frame for fitting to the body part; and
   a plurality of pivoting clamps mounted to the first frame, and forming constituent components of the first frame and not the second frame, and each having a clamping arm that is configured to pivot, relative to the outer, lateral edge of the first frame, to enable the clamping arm to engage with an outer, lateral edge of the upper flange of the second frame and with the outer, lateral edge of the first frame to clamp the first frame to the upper flange of the second frame when the first surface of the first frame is docked with the docking surface of the second frame, wherein the clamping arm comprises an upper clamping arm, a lower clamping arm, and a clamping space between the upper clamping arm and the lower clamping arm, and wherein the clamping arm is further configured such that, when engaged to clamp the outer, lateral edge of the first frame to the outer, lateral edge of the upper flange of the second frame, the upper clamping arm and the lower clamping arm do not extend inwards from the outer, lateral edge of the first frame beyond a boundary defined within a region between the outer, lateral edge and the inner, lateral edge of the first frame.

2. The mask structure of claim 1, wherein the first surface of the first frame comprises a lower surface, and wherein the lower surface further includes multiple retention pins that are configured to be inserted into corresponding holes of the upper flange of the second frame when the first frame is docked with the second frame.

3. The mask structure of claim 1, wherein the material is attached to the inner, lateral edge of the first frame, and wherein the plurality of pivoting clamps are mounted to the first frame along the outer, lateral edge of the first frame.

4. The mask structure of claim 1, wherein the shape comprises a U-shape, wherein the plurality of pivoting clamps comprises at least two pivoting clamps and wherein the at least two pivoting clamps are integrally mounted to the first frame at opposite sides of the U-shape of the first frame from one another.

5. The mask structure of claim 1, wherein the second frame comprises a half shell structure, wherein the upper flange extends around a portion of a perimeter of an upper edge of the second frame, and wherein the shape of the first frame conforms to the upper flange of the second frame.

6. The mask structure of claim 1, wherein the first frame includes a plurality of pivot holes disposed within the first frame, wherein each of the plurality of pivot holes establishes a respective rotation axis about which a different one of the plurality of pivoting clamps pivots, and wherein each of the plurality of pivoting clamps comprises a pivot pin that inserts into a respective pivot hole of the plurality of pivot holes.

7. The mask structure of claim 1, wherein, when each clamping arm pivots to engage with the outer, lateral edge of the upper flange of the second frame and with the outer, lateral edge of the first frame, the outer, lateral edge of the first frame and the outer, lateral edge of the upper flange of the second frame are clamped within the clamping space between the upper clamping arm and the lower clamping arm.

8. The mask structure of claim 1, wherein the first frame includes a plurality of pivot holes, that each establishes a respective rotation axis, disposed within the first frame near the outer, lateral edge of the first frame, wherein each pivot hole of the plurality of pivot holes extends through the first frame from an upper surface to a lower surface of the first frame, and wherein each of the plurality of pivoting clamps further comprises a pivot pin that, when mounted to the first frame, inserts into a respective pivot hole of the plurality of pivot holes and pivots within the respective pivot hole about the respective rotation axis.

9. The mask structure of claim 1, wherein the boundary defined within the region between the outer, lateral edge and the inner, lateral edge of the first frame comprises the boundary defined at approximately half of a distance between the outer, lateral edge and the inner, lateral edge across an upper surface of the first frame.

10. The mask structure of claim 1, wherein a portion of the clamping arm is partially disposed in a perimeter of the first frame when the clamping arm is disengaged from clamping the outer, lateral edge of the first frame to the outer, lateral edge of the upper flange of the second frame.

11. A medical treatment mask, comprising:
a mask frame comprising:
a first shape that fits around or over a patient's body part, and
at least one clamp mounted to the mask frame and configured to clamp the mask frame to a body part positioning device when the mask frame is docked with the body part positioning device, and
wherein the at least one clamp comprises at least one clamping arm configured to rotate about a rotation axis, disposed within the mask frame, to pivot the at least one clamping arm outwards away from, and inwards towards, an outer, lateral edge of the mask frame to enable the clamping arm to clamp the outer, lateral edge of the mask frame to an outer, lateral edge of an upper flange of the body part positioning device, and further wherein the at least one clamp is configured such that, when engaged to clamp the outer, lateral edge of the mask frame to the outer, lateral edge of an upper flange of the body part positioning device, the clamp does not extend outwards beyond a boundary defined by an outer perimeter of the mask frame; and
a sheet of material attached to the mask frame for fitting to the body part.

12. The medical treatment mask of claim 11, wherein the body part positioning device comprises a shell frame further comprising a second shape configured to receive the body part and wherein the upper flange extends around a perimeter of an upper edge of the shell frame.

13. The medical treatment mask of claim 11, wherein the at least one clamping arm comprises an upper clamping arm, a lower clamping arm, and a clamping space between the upper clamping arm and the lower clamping arm, wherein, when the at least one clamping arm is rotated about the rotation axis to pivot the at least one clamping arm inwards towards the mask frame, the outer, lateral edge of the mask frame and the outer, lateral edge of the upper flange of the body part positioning device are clamped within the clamping space between the upper clamping arm and the lower clamping arm.

14. The medical treatment mask of claim 11, wherein the mask frame further comprises a lower surface having multiple alignment pins for aligning the mask frame upon the body part positioning device when the mask frame is docked with the body part positioning device.

15. The medical treatment mask of claim 11, wherein the first shape comprises a U-shape, wherein the at least one clamp comprises at least two clamps and wherein the least two clamps are mounted to the mask frame at opposite sides of the U-shape of the mask frame from one another.

16. The medical treatment mask of claim 11, wherein the mask frame comprises the outer, lateral edge and an inner edge, wherein the sheet of material is attached to the inner edge of the mask frame, and wherein the at least one clamp is mounted to the mask frame along the outer, lateral edge of the mask frame.

17. The medical treatment mask of claim 11, wherein the mask frame comprises a lower surface, and wherein the lower surface includes multiple retention pins that are configured to insert into corresponding retention holes of an upper flange of the body part positioning device when the mask frame is docked with the body part positioning device.

18. The medical treatment mask of claim 11, wherein the mask frame includes at least one pivot hole, that establishes a respective rotation axis, disposed within the mask frame near the outer, lateral edge of the mask frame, wherein the at least one pivot hole extends through the mask frame from an upper surface to a lower surface of the mask frame, and wherein the at least one clamp further comprises a pivot pin that, when mounted to the mask frame, inserts into a respective pivot hole of the at least one pivot hole and pivots within the respective pivot hole about the respective rotation axis.

19. The medical treatment mask of claim 11, wherein the at least one clamp is partially disposed in the outer perimeter of the mask frame when the clamping arm is disengaged from clamping the outer, lateral edge of the mask frame to the outer, lateral edge of the upper flange of the body part positioning device.

20. A medical treatment mask, comprising:
a mask frame comprising:
 a first shape that fits around or over a patient's body part, wherein the mask frame comprises an outer, lateral edge and an inner, lateral edge, and
 a plurality of pivoting clamps mounted to the mask frame and configured to clamp the mask frame to a body part positioning device when the mask frame is docked with the body part positioning device, wherein the plurality of pivoting clamps form constituent components of the mask frame and not the body part positioning device,
  wherein each of the plurality of pivoting clamps comprises a clamping arm configured to rotate about a respective rotation axis, disposed within the mask frame, to pivot the clamping arm outwards away from, and inwards towards, an outer, lateral edge of the mask frame to enable the clamping arm to clamp the outer, lateral edge of the mask frame to an outer, lateral edge of an upper flange of the body part positioning device, wherein the clamping arm comprises an upper clamping arm, a lower clamping arm, and a clamping space between the upper clamping arm and the lower clamping arm, and wherein, when the clamping arm is rotated about the rotation axis to pivot the at least one clamping arm inwards towards the mask frame, the outer, lateral edge of the mask frame and the outer, lateral edge of the upper flange of the body part positioning device are clamped within the clamping space between the upper clamping arm and the lower clamping arm, and wherein, when the outer, lateral edge of the mask frame and the outer, lateral edge of the upper flange of the body part positioning device are clamped within the clamping space, the upper clamping arm and the lower clamping arm do not extend inwards from the outer, lateral edge of the mask frame beyond a boundary defined within a region between the outer, lateral edge and the inner, lateral edge of the mask frame, and
  wherein the mask frame includes a plurality of pivot holes, that each establishes the respective rotation axis, disposed within the mask frame near the outer, lateral edge of the mask frame, wherein each of the plurality of pivot holes extends through the mask frame from an upper surface to a lower surface of the mask frame, and wherein the plurality of clamps each further comprises a respective pivot pin that, when mounted to the mask frame, inserts into a respective pivot hole of the plurality of pivot holes and pivots within the respective pivot hole about the respective rotation axis; and
 a sheet of material attached to the mask frame for fitting to the body part.

21. The medical treatment mask of claim 20, wherein the boundary defined within the region between the outer, lateral edge and the inner, lateral edge of the mask frame comprises the boundary defined at approximately half of a distance between the outer, lateral edge and the inner, lateral edge across an upper surface of the mask frame.

22. The medical treatment mask of claim 20, wherein the clamping arm is partially disposed in a perimeter of the first frame when the clamping arm is disengaged from clamping the outer, lateral edge of the first frame to the outer, lateral edge of the upper flange of the second frame.

\* \* \* \* \*

UNITED STATES PATENT AND TRADEMARK OFFICE
CERTIFICATE OF CORRECTION

| | | |
|---|---|---|
| PATENT NO. | : 11,918,503 B2 | Page 1 of 1 |
| APPLICATION NO. | : 16/363441 | |
| DATED | : March 5, 2024 | |
| INVENTOR(S) | : Gregory Nephi Nordgren et al. | |

It is certified that error appears in the above-identified patent and that said Letters Patent is hereby corrected as shown below:

In the Claims

Column 14, Claim 15, Line 53 should read:
clamp comprises at least two clamps and wherein the at least Signed and Sealed this
Fourth Day of June, 2024

Katherine Kelly Vidal
*Director of the United States Patent and Trademark Office*